United States Patent
Okeke et al.

(10) Patent No.: US 10,329,593 B2
(45) Date of Patent: Jun. 25, 2019

(54) EFFICIENT PROCESS FOR PRODUCING SACCHARIDES AND ETHANOL FROM A BIOMASS FEEDSTOCK

(71) Applicant: AUBURN UNIVERSITY, Auburn, AL (US)

(72) Inventors: Benedict C. Okeke, Montgomery, AL (US); Ananda K. Nanjundaswamy, Vicksburg, MS (US)

(73) Assignee: Auburn University, Auburn, AL (US)

( * ) Notice: Subject to any disclaimer, the term of this patent is extended or adjusted under 35 U.S.C. 154(b) by 139 days.

(21) Appl. No.: 15/444,780

(22) Filed: Feb. 28, 2017

(65) Prior Publication Data
US 2017/0175153 A1  Jun. 22, 2017

Related U.S. Application Data

(62) Division of application No. 14/205,779, filed on Mar. 12, 2014, now Pat. No. 9,617,574.

(60) Provisional application No. 61/787,039, filed on Mar. 15, 2013.

(51) Int. Cl.
| | |
|---|---|
| *C12P 19/14* | (2006.01) |
| *C12P 19/02* | (2006.01) |
| *C12P 7/14* | (2006.01) |
| *C12R 1/885* | (2006.01) |
| *C12N 9/24* | (2006.01) |
| *C12P 7/10* | (2006.01) |
| *A23K 20/10* | (2016.01) |
| *A01N 63/04* | (2006.01) |
| *B09C 1/10* | (2006.01) |
| *C12N 9/42* | (2006.01) |

(52) U.S. Cl.
CPC .............. *C12P 19/14* (2013.01); *A01N 63/04* (2013.01); *A23K 20/10* (2016.05); *B09C 1/105* (2013.01); *C12N 9/2402* (2013.01); *C12N 9/248* (2013.01); *C12N 9/2437* (2013.01); *C12N 9/2445* (2013.01); *C12N 9/2482* (2013.01); *C12P 7/10* (2013.01); *C12P 7/14* (2013.01); *C12P 19/02* (2013.01); *C12R 1/885* (2013.01); *C12Y 302/01004* (2013.01); *C12Y 302/01008* (2013.01); *C12Y 302/01021* (2013.01); *C12Y 302/01037* (2013.01); *B09C 2101/00* (2013.01); *Y02E 50/16* (2013.01); *Y02P 20/52* (2015.11)

(58) Field of Classification Search
CPC combination set(s) only.
See application file for complete search history.

(56) References Cited

U.S. PATENT DOCUMENTS

| | | | |
|---|---|---|---|
| 4,626,029 A | 12/1986 | Eveleigh et al. | |
| 4,840,903 A | 6/1989 | Wu et al. | |
| 5,753,484 A | 5/1998 | Ward et al. | |
| 5,837,515 A | 11/1998 | Suominen et al. | |
| 5,981,233 A | 11/1999 | Ringpfeil | |
| 6,228,630 B1 | 5/2001 | Kofod et al. | |
| 7,419,809 B2 | 9/2008 | Foody et al. | |
| 7,494,792 B2 | 2/2009 | Warzywoda et al. | |
| 7,754,456 B2 | 7/2010 | Penttila et al. | |
| 7,923,236 B2 * | 4/2011 | Gusakov ............ C11D 3/38645 162/174 |
| 2002/0164730 A1 | 11/2002 | Ballesteros Percides et al. | |
| 2003/0054518 A1 | 3/2003 | Saloheimo et al. | |
| 2003/0180900 A1 | 9/2003 | Lantero | |
| 2005/0208623 A1 | 9/2005 | Baldwin et al. | |
| 2006/0014260 A1 | 1/2006 | Fan et al. | |
| 2008/0057541 A1 | 3/2008 | Hill et al. | |
| 2008/0076159 A1 | 3/2008 | Baez-Vasquez et al. | |
| 2008/0193982 A1 | 8/2008 | Smith et al. | |
| 2009/0042266 A1 | 2/2009 | Vehmaanpera et al. | |
| 2009/0053777 A1 | 2/2009 | Hennessey et al. | |
| 2009/0061484 A1 | 3/2009 | Scott et al. | |
| 2009/0117634 A1 | 3/2009 | Bradley et al. | |
| 2009/0203087 A1 | 8/2009 | Baldwin et al. | |
| 2009/0203101 A1 | 8/2009 | Breneman et al. | |

(Continued)

FOREIGN PATENT DOCUMENTS

| | | |
|---|---|---|
| EP | 1130085 | 2/2001 |
| EP | 2281028 | 10/2009 |

(Continued)

OTHER PUBLICATIONS

Barnett et al (Cloning and amplification of the gene encoding an extracellular beta-glucosidase from Trichoderma reesei: evidence for improved rates of saccharification of cellulosic substrates. Nature Biotechnology 1991, vol. 9, p. 562-567).*

(Continued)

*Primary Examiner* — Kagnew H Gebreyesus
(74) *Attorney, Agent, or Firm* — Gardner Groff Greenwald & Villanueva, PC

(57) ABSTRACT

Described herein is a process for producing saccharides and ethanol from biomass feedstock that includes (a) producing an enzyme composition by culturing a fungal strain(s) in the presence of a lignocellulosic medium, (b) using the enzyme composition to saccharify the biomass feedstock, and (c) fermenting the saccharified biomass feedstock to produce ethanol. The process is scalable and, in certain aspects, is capable of being deployed on farms, thereby allowing local production of saccharides and ethanol and resulting in a reduction of energy and other costs for farm operators. Optional steps to improve the biomass-to-fuel conversion efficiency are also contemplated, as are uses for byproducts of the process described herein.

12 Claims, 6 Drawing Sheets

Specification includes a Sequence Listing.

(56) References Cited

U.S. PATENT DOCUMENTS

| | | |
|---|---|---|
| 2009/0209009 A1 | 8/2009 | Tolan et al. |
| 2009/0325240 A1 | 12/2009 | Daniell |
| 2010/0068768 A1 | 3/2010 | Tolan et al. |
| 2010/0279361 A1 | 11/2010 | South |
| 2010/0304437 A1 | 12/2010 | Garner et al. |
| 2010/0304438 A1 | 12/2010 | Scott et al. |
| 2010/0313882 A1 | 12/2010 | Dottori et al. |
| 2011/0045544 A1 | 2/2011 | Vehmaanpera et al. |
| 2011/0129889 A1 | 6/2011 | Inamdar et al. |
| 2011/0171710 A1 | 7/2011 | Yu et al. |

FOREIGN PATENT DOCUMENTS

| | | |
|---|---|---|
| EP | 2307555 | 3/2010 |
| EP | 2432889 | 11/2010 |
| EP | 2188381 | 12/2011 |
| WO | 2008058362 | 5/2008 |

OTHER PUBLICATIONS

Wisner, Ag Marketing Resource Center (2012) Article date Dec. 11, 2012 http://www.extension.iastate.edu/agdm/crops/outlook/dgsbalancesheet.pdf.

Ananda N, Vadlani PV, Vara Prasad PV. Drought and heat stressed grain sorghum (Sorghum bicolor) does not affect the glucose and ethanol production. Industrial Crops and Products (2011) 33:779-782.

Renewable Fuels Association (2012) http://www.ethanolrfa.org/pages/statistics.

Okeke B.C. and Lue J, Characterization of a Defined Cellulolytic and Xylanolytic Bacterial Consortium for Bioprocessing of Cellulose and Hemicelluloses. Applied Biochemistry and Biotechnology (2011) 163: 869-881.

Saha BC, Iten LB, Cotta MA, Wu YV, Dilute acid pretreatment, enzymatic saccharification and fermentation of rice hulls to ethanol. Biotechnology Progress (2005) 21:816-822.

Schnepf R and Yacobucci BD (2092) renewable fuel standard (RFS): Overview and issues. Congressional Research Service. 7-5700.

U.S.-Department of Energy (2005) "Billion Ton Study": Biomass as feedstock for a bioenergy and bioproducts industry: The technical feasibility of a billion-ton annual supply. Perlack RD, Wright LL, Turhollow AF, Graham RL, Stokes BJ, Erbach DC. DOE/GO-102995-2135.

U.S. Department of Energy (2011) U.S. Billion Ton Update Biomass supply for a bioenergy and bioproducts industry. RD Perlack and BJ Stokes (Leads) ORNL/TM-2011/224. Oak Ridge National Laboratory, Oak Ridge, TN. 227p.

Andrew Paulk, Ananda Nanjundaswamy, Benedict Okeke (Apr. 2, 2013). Liquid chromatography-mass spectrometry (LC-MS) profiling of oligosaccharide intermediates in lignocellulosic biomass saccharification. Auburn Research Week Apr. 1-4, 2013, Auburn, AL.

Christopher Starr, Ananda Nanjundaswamy, Benedict Okeke (Apr. 2, 2013). Enhanced feedstock saccharification by crude fungal enzyme concentrated by tangential flow filtration, Auburn Research Week Apr. 1-4, 2013, Auburn, AL.

Christopher Starr, Ananda Nanjundaswamy, Benedict Okeke (Apr. 2, 2013). Single-step saccharification of switchgrass is more efficient than repeated saccharification in cellulosic biofuel production, Auburn Research Week Apr. 1-4, 2013, Auburn, AL.

Andrew Paulk, Ananda Nanjundaswamy, Benedict Okeke (Apr. 12, 2013). Lignocellulosic oligosaccharide characterization using liquid chromatography-mass spectrometry (LC-MS). AUM Sciences Undergraduate Research Symposium Apr. 12, 2013, Montgomery, AL.

Christopher Starr, Ananda Nanjundaswamy, Benedict Okeke (Apr. 12, 2013). Tangential flow filtration effectively concentrates crude fungal enzyme used in feedstock saccharification. AUM Sciences Undergraduate Research Symposium Apr. 12, 2013, Montgomery, AL.

Christopher Starr, Ananda Nanjundaswamy, Benedict Okeke (Apr. 12, 2013). Comparison of single-step and repeated-saccharification of switchgrass in cellulosic biofuel production. AUM Sciences Undergraduate Research Symposium Apr. 12, 2013, Montgomery, AL.

Ananda, B (Jun. 10-13, 2013). Development of fungal crude enzyme-commercial enzyme cocktail for potential cost reduction of cellulosic biomass saccharification. Fuel Ethanol Workshop (FEW), St. Louis, MO, Jun. 10-13, 2013.

Ananda, Potential cost reduction of cellulosic biomass saccharification by fungal crude enzyme—commercial enzyme cocktail. Clean Technology Conference and Expo, Washington, DC, May 12-16, 2013.

Nanjundaswamy A, Starr C, Okeke B (May 19, 2013). Processing of Biomass-Saccharifying Enzymes by Sand Filtration for 'Farm Deployable Microbial Bioreactor' Laboratory Model. American Society of Microbiology, Denver, CO, May 18-21, 2013.

Okeke B, Nanjundaswamy A, Deravi Y, Peaks S, Prescott A, Hall R (Aug. 12, 2012). Biomass saccharification by cellulolytic-xylanolytic enzymes complex of newly isolated fungal strains. Society for Industrial Microbiology, Annual Meeting and Exhibition, Washington DC, Aug. 12-16, 2012.

Ananda (Apr. 3, 2012). 'All-in-one' bioprocessing strategy for cellulosic ethanol production: a laboratory model bioreactor study. Auburn University Research Week, Auburn, AL, Apr. 2-4, 2012.

Ananda, 'Ail-in-one' bioprocessing strategy for cellulosic ethanol production: a laboratory model bioreactor study. International Biomass Conference and Expo, Denver, Colorado, Apr. 16-19. 2012;.

Okeke B, Prescott A, Deravi Y, Bishop J, Peaks S, Sawyer L, Nanjundaswamy A, Hall R (Apr. 3, 2012) Screening of xylose-utilizing yeasts and bacteria for xylose fermentation to ethanol. Auburn University Research Week, Auburn, AL, Apr. 2-4, 2012.

Nanjundaswamy A, Okeke B (Jul. 24, 2011. Optimization of culture parameters for production of cellulolytic and xylanolytic enzymes from a new Trichoderma species SG2. Society of Industrial Microbiology (SIM) Annual Meeting and Exhibition, New Orleans, LA, Jul. 24-28, 2011.

Okeke BC, Deravi Y, Prescott A, Bishop J, Sawyer L, Peaks S, Nanjundaswamy A, Hall, R (Jul. 24, 2011). Screening of xylose-utilizing yeasts from soil-decaying biomass composite samples and fruits for ethanol production. Society for Industrial Microbiology, Annual Meeting, New Orleans, LA, Jul. 24-28, 2011.

Benedict Okeke, Yasi Deravi and Jue Lu (Aug. 1, 2010) Cellulolytic and Xylanolytic Enzymes Potential of Fungi from Soil Beneath Decaying Biomass. Society of Industrial Microbiology. 60th Annual Meeting, San Francisco, CA, Aug. 1-5, 2010.

Peterson, Trichoderma reesei RUT-C30-Thirty Years of Strain Improvement, Microbiology, (2012), vol. 158, 58-68.

Wyman, Coordinated development of leading biomass pretreatment technologies, Biosource Technolgy 96, 2005, 1959-1966.

Epplin, Cost to Produce and Deliver Switchgrass Biomass to an Ethanol-Conversion Facility in the Southern Plains of the United States, 1996, Biomass and Bioenergy vol. 11, No. 6, 459-467.

Mielenz, Ethanol production from biomass: technology and commercialization status, Current Opinion in Microbiology, 2001, 4:324-329.

Faculty Forum Sessions, Auburn University Research Week 2012.

Ananda, Evaluation of drought and head stressed grain sorghum (Sorghum bicolor) for ethanol production, Industrial Crops and Products, 2011, vol. 33, No. 6, 779-782.

Alvira, Pretreatment technologies for an efficient bioethanol production process based on enzymatic hydrolysis: A review, Bioresource Technology 101 (2010), 4851-4861.

Andric, Reactor design for minimizing product inhibition during enzymatic lignocellulose hydrolysis: 1. Significance and mechanism of cellobiose and glucose inhibition on cellulolytic enzymes, Biotechnology Advances 28 (2010), 308-324.

Saha, Dilute acid pretreatment, enzymatic saccharification and fermentation of wheat straw to ethanol, Process Biochemistry 40 (2005)3693-3700.

(56) References Cited

OTHER PUBLICATIONS

Roslan, AM et al.; "Production of bioethanol from rice straw using cellulase by local *Aspergillus* sp.," Int. J. Agr. Res.;.

* cited by examiner

SEQUENCE LISTING

<160> NUMBER OF SEQ ID NOS: 9

<210> SEQ ID NO 1
<211> LENGTH: 580
<212> TYPE: DNA
<213> ORGANISM: Trichoderma SG2

<400> SEQUENCE: 1

| gatcgaacgt | gcatcctcct | gatcgaggtc | acatttccaa | gttgggtgtt | taacggctgt | 60 |
| ggacccgccg | cgctcccgat | gccagtgtgc | aaactactgc | gcaggagagg | ctgcagcgag | 120 |
| accgccactg | tatttcggag | acggccaccg | ccaaggcagg | gccgatcccc | aaccccacc | 180 |
| ccccggaggg | gttcgagggt | tgaaatgacc | ctcggacaag | catgcccgcc | agaatactgg | 240 |
| cgggcgcaat | gtgcgttcaa | agattcgatg | attcactgaa | ttctgcaatt | cacattactt | 300 |
| atctcatttc | cctgctttct | tcatcgatgc | cctaaccaag | atatccgttg | ttgaaagttt | 360 |
| tgattcattt | tccaaacgcc | ggggtaggc | gccgaggggc | tcagattata | aaaaaaaccc | 420 |
| ccgaggggt | atacaataac | agttttggtt | ggtcctcccg | cgggcgcctt | ggtccggggc | 480 |
| tgcgacgcaa | ccggggcaga | gatcccgccg | aggcaacagt | tggtaacgt | tcacattggg | 540 |
| tttgggagtt | gtaaactcgg | taatgatccc | tccgcactac | | | 580 |

<210> SEQ ID NO 2
<211> LENGTH: 358
<212> TYPE: DNA
<213> ORGANISM: Trichoderma SG2

<400> SEQUENCE: 2

| gcatcgatga | agaacgcagc | gaaatgcgat | aagtaatgtg | aattgcagaa | ttcagtgaat | 60 |
| catcgaatct | ttgaacgcac | attgcgcccg | ccagtattct | ggcgggcatg | cctgtccgag | 120 |
| cgtcatttca | accctcgaac | ccctcggggg | ggtcggcgtt | ggggatcggc | cctgccttgg | 180 |
| cggtggccgt | ctccgaaata | cagtggcggt | ctcgccgcag | cctctcctgc | gcagtagttt | 240 |
| gcacactcgc | atcgggagcg | cggcgcgtcc | acagccgtta | aacacccaac | ttctgaaatg | 300 |
| ttgacctcgg | atcaggtagg | aatacccgct | gaacttaagc | atatcaataa | gcggagga | 358 |

<210> SEQ ID NO 3
<211> LENGTH: 700
<212> TYPE: DNA
<213> ORGANISM: Trichoderma SG2

<400> SEQUENCE: 3

| catcataagt | tcgattagtc | tttcgcccca | tgcccatatt | tgacgatcga | tttgcacgtc | 60 |
| agaaccgctg | cgagcctcca | ccagagtttc | ctctggcttc | accctataca | ggcatagttc | 120 |
| accttctttc | gggtccggcc | ccgtatgctc | ttactcaaat | ccatccgaga | acatcaggat | 180 |
| cggtcgatga | tgcgccgaag | ctctcacctg | cgttcacttt | cattacgcgt | aggggtttga | 240 |
| cacccgaaca | ctcgcatacg | aagacgactc | cttggtccgt | gtttcaagac | gggtcgctgg | 300 |
| tgaccattac | gccagcatcc | ttgcagatgc | gcggtcctca | gtccaccgca | gggtattatg | 360 |
| caacgggcta | taacactccc | ggaggagcca | cgttcccgaa | gccttttcc | ccgcgacga | 420 |
| actgatgctg | gcctagacgc | ggcgaagtgc | accggagaga | accccggatg | atccgccgcg | 480 |
| cccaagtctg | gtcacaagcg | cttcccttc | aacaatttca | cgtactattt | aaccctcttt | 540 |
| tcaaggtgct | tttcatcttt | cgatcactct | acttgtgcgc | tatcggtctc | tggccaatat | 600 |
| ttagctttag | aagacatata | cctcccattt | tgagcagcat | tcccaaacta | ctcgactcgt | 660 |

```
cgaaggagct ttacagaggc tcggcggcca gccagacggg              700
```

<210> SEQ ID NO 4
<211> LENGTH: 649
<212> TYPE: DNA
<213> ORGANISM: Trichoderma SG4

<400> SEQUENCE: 4

```
ggctccataa ggaggctgca tgatcgaggt cacatttcag aagttgggtg tttaacggct     60
gtggacgcgc cgcgctcccg atgcgagtgt gcaaactact gcgcaggaga ggctgcggcg    120
agaccgccac tgtatttcgg agacggccac cgccaaggca gggccgatcc ccaaccccga    180
ccccccggag gggttcgagg gttgaaatga cgctcggaca ggcatgcccg ccggaatact    240
ggcgggcgca atgtgcgttc aaagattcga tgattcactg aattctgcaa ttcacattac    300
ttatcgcatt tcgctgcgtt cttcatcgat gccagaacca agagatccgt tgttgaaagt    360
tttgattcat tttccaaacg cctacgagag gcgccgagaa ggctcagatt ataaaaaaac    420
ccgcgagggg gtatacaata agagttttgg ttggtcctcc ggcggcgcc ttggtccggg     480
gctgctacgc acccggggca gagatcccgc cgaggcaaca gtttggtaac gttcacattg    540
ggtttgggag ttgtaaactc ggtaatgatc cctcctcacg tccaacaatt atctactaca    600
tccctcgggt gcgtataggg acaacgactt ctgtggctgc cctctcac                649
```

<210> SEQ ID NO 5
<211> LENGTH: 358
<212> TYPE: DNA
<213> ORGANISM: Trichoderma SG4

<400> SEQUENCE: 5

```
gcatcgatga agaacgcagc gaaatgcgat aagtaatgtg aattgcagaa ttcagtgaat     60
catcgaatct ttgaacgcac attgcgcccg ccagtattct ggcgggcatg cctgtccgag    120
cgtcatttca accctcgaac ccctccgggg ggtcggcgtt ggggatcggc cctgccttgg    180
cggtggccgt ctccgaaata cagtggcggt ctcgccgcag cctctcctgc gcagtagttt    240
gcacactcgc atcgggagcg cggcgcgtcc acagccgtta aacacccaac ttctgaaatg    300
ttgacctcgg atcaggtagg aatacccgct gaacttaagc atatcaataa gcggagga     358
```

<210> SEQ ID NO 6
<211> LENGTH: 900
<212> TYPE: DNA
<213> ORGANISM: Trichoderma SG4

<400> SEQUENCE: 6

```
agagggagta ggtcgattag tctttcgccc catgcccata tttgacgatc gatttgcacg     60
tcagaaccgc tgcgagcctc accagagtt tcctctggct tcaccctata caggcatagt    120
tcaccttctt tcgggtccgg ccccgtatgc tcttactcaa atccatccga gaacatcagg    180
atcggtcgat gatgcgccga agctctcacc tgcgttcact ttcattacgc gtaggggttt    240
gacacccgaa cactcgcata cgaagacgac tccttggtcc gtgtttcaag acgggtcgct    300
ggtgaccatt acgccagcat ccttgcagat gcgcggtcct cagtccaccg cagggtatta    360
tgcaacgggc tataacactc ccggaggagc cacgttcccg aagcctttt ccccccgcgac    420
gaactgatgc tggcctagac gcggcgaagt gcaccggaga gaaccccgga tgatccgccg    480
cgcccaagtc tggtcacaag cgcttcccctt tcaacaattt cacgtactat ttaaccctct    540
```

```
tttcaaggtg cttttcatct ttcgatcact ctacttgtgc gctatcggtc tctggccaat    600
atttagcttt agaagacata tacctcccat tttgagcagc attcccaaac tactcgactc    660
gtcaaaggag ctttacagag gctcggcggc cagccagacg gggctctcac cctctgtggc    720
gtcccgttcc agggaactcg gcggcacct caccaaaagc atcctctaca aattacaact    780
cgggccctag ggaccagatt tcaaatttga gctgttgccg cttcactcgc cgttactggg    840
gcaatccctg ttggtttctt ttcctccgct tattgatatg cttaagtccc tcggggtag    900
```

```
<210> SEQ ID NO 7
<211> LENGTH: 880
<212> TYPE: DNA
<213> ORGANISM: Trichoderma FS5A

<400> SEQUENCE: 7
cgtgtttaag gtcgattagt ctttcgcccc atgcccatat ttgacgatcg atttgcacgt     60
cagaaccgct gcgagcctcc accagagttt cctctggctt caccctatac aggcatagtt    120
caccttcttt cgggtccggc cccgtatgct cttactcaaa tccgtccgag aacatcagga    180
tcggtcgatg atgcgccgaa gctctcacct gcgttcactt tcattacgcg tagggggtttg   240 acacccgaac actcgcatac gaagacgact ccttggtccg tgtttcaaga cgggtcgctg    300
gtgaccatta cgccagcatc cttgcagatg cgcggtcctc agtccaccgc agggtattat    360
gcaacgggct ataacactcc cggaggagcc acgttcccga agcctttttc ccccgcgacg    420
aactgatgct ggcctagacg cggcgaagtg caccggagag aaccccggat gatccgccgc    480
gcccaagtct ggtcacaagc gcttcccttt caacaatttc acgtactatt taaccctctt    540
ttcaaggtgc ttttcatctt tcgatcactc tacttgtgcg ctatcggtct ctggccaata    600
tttagcttta agacatat acctcccatt ttgagcagca ttcccaaact actcgactcg     660
tcgaaggagc tttacagagg ctcggtggcc agccagacgg ggctctcacc ctctgtggcg    720
tcccgttcca gggaactcgg gcggcacctc accaaaagca tcctctacaa attacaactc    780
ggaccccgag gggccagatt tcaaatttga gctgttgccg cttcactcgc cgttactggg    840
gcgatccctg ttggtttctt ttcctccgct tattgatatg                          880
```

```
<210> SEQ ID NO 8
<211> LENGTH: 355
<212> TYPE: DNA
<213> ORGANISM: Trichoderma FS5A

<400> SEQUENCE: 8
gcatcgatga agaacgcagc gaaatgcgat aagtaatgtg aattgcagaa ttcagtgaat     60
catcgaatct ttgaacgcac attgcgcccg ccagtattct ggcgggcatg cctgtccgag    120
cgtcatttca accctcgaac cctccgggg gtcggcgtt ggggatcggc cctttacggg     180 gccggcccg aaatacagtg gcggtctcgc cgcagcctct cctgcgcagt agtttgcaca    240
ctcgcatcgg gagcgcggcg cgtccacagc cgttaaacac cccaaacttc tgaaatgttg   300
acctcggatc aggtaggaat acccgctgaa cttaagcata tcaataagcg gagga         355
```

```
<210> SEQ ID NO 9
<211> LENGTH: 355
<212> TYPE: DNA
<213> ORGANISM: Penicillium FS22A

<400> SEQUENCE: 9
gcatcgatga agaacgcagc gaaatgcgat aagtaatgtg aattgcagaa ttcagtgaat     60
```

-continued

```
catcgagtct ttgaacgcac attgcgcccc ctggtattcc gggggggcatg cctgtccgag    120 cgtcattgct gccctcaagc acggcttgtg tgttgggccc ccgcccccg gctcccgggg      180 ggcgggcccg aaaggcagcg gcggcaccgc gtccggtcct cgagcgtatg gggcttcgtc    240
acccgctctg taggcccggc cggcgcccgc cggcgacccc cctcaatctt tctcaggttg    300
acctcggatc aggtagggat acccgctgaa cttaagcata tcaataagcg gagga         355
```

EFFICIENT PROCESS FOR PRODUCING SACCHARIDES AND ETHANOL FROM A BIOMASS FEEDSTOCK

CROSS REFERENCE TO RELATED APPLICATIONS

This application is a divisional application of U.S. non-provisional application Ser. No. 14/205,779, filed on Mar. 12, 2014, which claims priority upon U.S. provisional application Ser. No. 61/787,039, filed Mar. 15, 2013. This application is hereby incorporated by reference in its entirety for all of its teachings.

STATEMENT REGARDING FEDERALLY SPONSORED RESEARCH OR DEVELOPMENT

The subject matter described herein was developed with funding provided by the United States Department of Energy (U.S. DOE, DE-EE0003132/000). The U.S. Government has rights in the invention.

BACKGROUND

Presently, U.S. energy consumption statistics are overwhelming: about 20 million barrels of oil a day are used, of which 70% go toward transportation. With oil prices averaging $100 per barrel, the U.S. spends about 2 trillion dollars a year on petroleum-based energy. More than half of the oil used is imported, so the United States is still "energy dependent." Less than 10% of the U.S.'s energy comes from renewable resources; of that, 2% is from biofuels.

U.S. federal policy on biofuel usage is outlined in the Renewable Fuel Standard (RFS) which provides the minimum biofuel volume to be blended into the national fuel supply each year. Initially, RFS 1—also known as the EPA Act of 2005—mandated a minimum use of 4 billion gallons of biofuel in 2006 and, by 2012, a minimum of 7.5 billion gallons. RFS 2—also known as the EPA Act of 2007—mandated minimum biofuel blending volume of 9 billion gallons by 2008 and 36 billion gallons by 2022. Of this, corn biofuel is limited to a maximum of 15 billion gallons; however, a minimum of 16 billion gallons of cellulosic biofuel is mandated.

The United States is the world's largest producer of fuel ethanol and corn is the primary feedstock for ethanol production. In January 2012, 14.9 billion gallons of ethanol were produced in the U.S. and 42.5 million short tons of coproduct—namely dried distillers grain with solubles—were produced. As the U.S. is close to producing the maximum volume of corn biofuel mandated by RFS 2, the efficient production and commercialization of cellulosic ethanol are subjects of intense research. Although some agronomic hurdles to the production of lignocellulosic feedstock exist, the most significant limitations to commercial production of cellulosic ethanol are associated with the costs of enzymes for saccharification, logistics, and biomass processing. For example, due to low bulk density and high volumes, transportation of biomass over long distances is uneconomical. Enzymes for large-scale biomass saccharification are estimated to cost $2-$3 per gallon of biofuel. Enzymes are used at high loading levels as the conversion efficiency of these enzymes is much lower than the starch hydrolyzing enzymes used in producing ethanol from corn.

β-glucosidases and β-xylosidases are extremely important terminal enzymes involved in producing fermentable sugars such as glucose and xylose from non-fermentable intermediates such as cellobiose, cello-oligosaccharides, xylobiose, and xylo-oligosaccharides. Strains of *Trichoderma* fungus are the most common cellulase-producing microorganisms currently employed in an industrial setting. However, commercial strains typically lack the high levels of β-glucosidases required for efficient hydrolysis of cellobiose. Commercial cellulose preparations are typically supplemented with β-glucosidases to increase the rate of cellulose hydrolysis. High levels of β-glucosidases increase conversion of lignocellulosic material into glucose and decrease the inhibitory effect of cellobiose on endo- and exo-cellulases, in turn leading to greater ethanol yield. β-glucosidases also serve several other important biological functions including, but not limited to, cellulase induction, deglycosylation of isoflavone glycosides, and synthesis of industrially-important glycosidic compounds. Currently, the *Trichoderma* strain most commonly used in industry is the extensively genetically-manipulated *Trichoderma reesei* RUT-C30. However, this strain, while hypercellulolytic in nature, exhibits relatively low levels of β-glucosidase and β-xylosidase activity.

Agricultural residues like corn stover and wheat straw, bioenergy crops, and residues from the forestry and logging industries, all constitute biomass feedstock for ethanol, and many of these are abundant on local farms. The U.S. has the capacity to produce about 1.3 billion dry tons of sustainably collectable biomass annually, allowing the country to meet a third of its energy demand by 2030 while also continuing to meet food, feed, and export demands according to the US-DOE Billion ton study (2005) and Billion ton update (2011). These estimates take into consideration the sustainable production of lignocellulosic feedstock at baseline and under high yield scenarios for energy crops by state and county, secondary resources by state, and primary herbaceous non-woody and woody crops by county. For example, if biomass availability at high yield was assumed at $60 per dry ton, then 1 billion dry tons of biomass would be easily available by 2022 at a 4% growth rate, which would provide close to a trillion kilowatts of power by 2022. The U.S. has about 922 million acres of farmland. In 2006, average farm size by state varied from as high as 2,610 acres in Arizona to 71 acres in Rhode Island.

Presently, the U.S. generates about 400 to 600 million dry tons of biomass annually for potential fuel production. Transport of this biomass to fuel processing facilities is costly and current methods for processing biomass into fuel are cost-prohibitive and beyond the technical capabilities and resources of farm workers, owners, and managers.

SUMMARY

Described herein is a process for producing saccharides and ethanol from biomass feedstock that includes (a) producing an enzyme composition by culturing a fungal strain(s) in the presence of a lignocellulosic medium, (b) using the enzyme composition to saccharify the biomass feedstock, and (c) fermenting the saccharified biomass feedstock to produce ethanol. The process is scalable and, in certain aspects, is capable of being deployed on farms, thereby allowing local production of saccharides and ethanol and resulting in a reduction of energy and other costs for farm operators. Optional steps to improve the biomass-to-fuel conversion efficiency are also contemplated, as are uses for byproducts of the process described herein.

The advantages of the materials, methods, and devices described herein will be set forth-in part in the description which follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
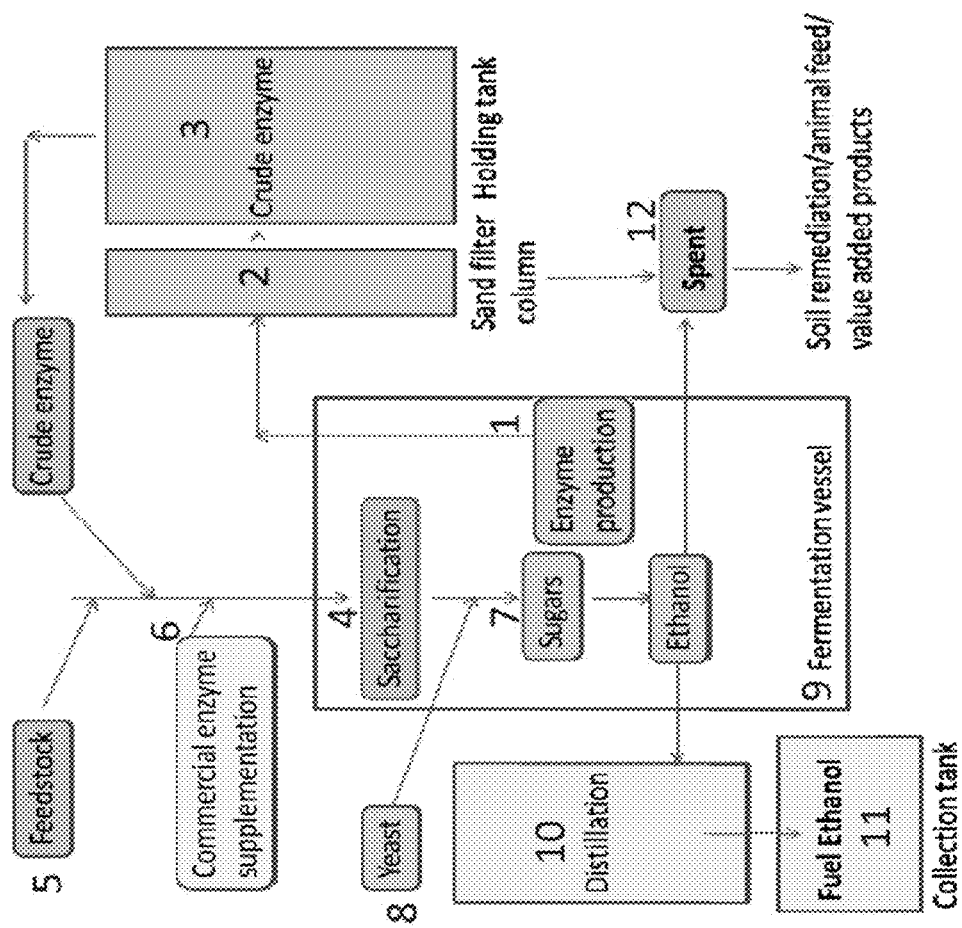
FIG. 1 is a schematic of bioreactor processes for performing the methods described herein.

The compositions, methods, and articles described herein can be understood more readily by reference to the following detailed description. It is also to be understood that the terminology used herein is for the purpose of describing particular aspects only and is not intended to be limiting.

It must be noted that, as used in the specification and the appended claims, the singular forms "a," "an," and "the" include plural referents unless the context clearly dictates otherwise. Thus, for example, reference to "an enzyme" includes mixtures of two or more enzymes.

"Optional" or "optionally" means that the subsequently described event or circumstance can or cannot occur and that the description includes instances where the event or circumstance occurs and instances where it does not. For example, the phrase "optionally includes paper powder" means that paper powder can or cannot be included.

As used herein, the term "about" is used to provide flexibility to a numerical range endpoint by providing that a given value may be "a little above" or "a little below" the endpoint without affecting the desired result.

"Biomass" refers to material from a biological source, such as, for example, a plant, that can be converted into a source of energy. In some aspects, the energy source is renewable.

"Lignocellulosic material" is any dry material from a plant and includes, at a minimum, carbohydrates such as cellulose and hemicellulose and/or polyphenolic compounds such as lignin. Lignocellulosic material may be obtained from agricultural residues such as, for example, corn stover or wheat straw; from byproducts of wood or paper processing such as, for example, sawdust or paper mill discards; from crops dedicated to biomass production; from municipal waste such as, for example, paper; or a combination thereof. Lignocellulosic material may also contain xylan, starch, pectin, and the like. A "lignocellulosic medium" is a culture medium that includes any of the lignocellulosic material defined herein. In other aspects, a lignocellulosic medium is purchased from a commercial source.

As used herein, a "bioenergy crop" or "bioenergy grass" refers to an agricultural crop that is grown specifically for purposes of energy production. In some aspects, a bioenergy crop is a non-food crop such as, for example, a grass such as switchgrass or gammagrass. In other aspects, a bioenergy crop is a plant that is normally a food crop. For example, when corn grains are used for ethanol, it is referred to as corn ethanol. However, parts of the plant left behind after harvesting the grains that are not edible are known as feedstock and used for the production of lignocellulosic ethanol.

As used herein, "residue" refers to byproducts of processes such as, for example, agricultural, forestry, sawmill, paper mill, or similar processes. "Residue" in this context can include, for example, wood chips, sawdust, branches, stumps, non-food lignocellulosic material from food crops including corn stover and wheat straw, paper mill waste, waste carbohydrates, animal manure, post-consumer paper products, and combinations thereof. "Waste carbohydrates" or "high sugar waste" refers to fermentable sugars that are byproducts of processing lignocellulosic material or other complex polysaccharides for use in the food industry.

"Feedstock" as used herein is the starting raw material from which ethanol is ultimately made. In some aspects, feedstock is composed of residue as defined above. In other aspects, a bioenergy crop or bioenergy grass can be used as feedstock. In some aspects, feedstock can contain cellulose, starch, or another glucan; hemicellulose; pectin; lignin; xylan; or a combination thereof. A "biomass feedstock" is a feedstock composed of biomass as defined above. In certain aspects, a biomass feedstock includes residue, a bioenergy crop, or lignocellulosic material as defined above.

As used herein, "biofuel" refers to a fuel source that stores energy that is ultimately of biological origin. Biofuels can include fuel alcohols such as, for example, ethanol.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range if each numerical value and sub-range was explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, etc., as well as 1, 2, 3, 4, and 5, individually. The same principle applies to ranges reciting only one numerical value as a minimum or a maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a fungal species is disclosed and discussed and a number of different biomass feedstocks are discussed, each and every combination of fungal species and biomass feedstock that is possible is specifically contemplated unless specifically indicated to the contrary. For example, if a class of molecules A, B, and C are disclosed, as well as a class of molecules D, E, and F, and an example of a combination A+D is disclosed, then even if each is not individually recited, each is individually and collectively contemplated. Thus, in this example, each of the combinations A+E, A+F, B+D, B+E, B+F, C+D, C+E, and C+F, are specifically contemplated and should be considered disclosed from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of this disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Pretreatment Protocols

In one aspect, a biomass feedstock is pretreated prior to enzyme saccharification. In a further aspect, the pretreatment protocol can include such as, for example, heat and/or autoclave pretreatment, acid pretreatment, alkali pretreatment, pretreatment with an organic solvent, and combinations thereof. In this aspect, the organic solvent can be acetone or ethanol. In one aspect, the biomass feedstock is treated with acid. In a further aspect, the acid is sulfuric acid or phosphoric acid. In this aspect, the concentration of sulfuric acid can be from about 0.5% (v/v) to about 2% (v/v), and the concentration of phosphoric acid can be about 85%. In one aspect, after treatment with phosphoric acid, the biomass feedstock is further treated with acetone. In another aspect, after treatment with phosphoric acid, the biomass feedstock is further treated with ethanol. In this aspect, the ethanol concentration can be 95% (v/v). In another aspect, the biomass feedstock is treated with base (alkali). In this aspect, the base can be sodium hydroxide and the concentration of base can be from about 0.5% (w/v) to about 2% (w/v). In one aspect, the biomass feedstock is contacted with acid prior to being contacted with alkali. In another aspect, the biomass feedstock is contacted with alkali prior to being contacted with acid. In still another aspect, the biomass feedstock is treated with heat. In one aspect, the heat is applied in an autoclave. Further in this aspect, the autoclave temperature is about 121° C. In yet another aspect, the biomass feedstock is not pretreated. Exemplary procedures for pretreatment are provided in the Examples.

In some aspects, following pretreatment, the biomass feedstock is drained of liquid. In one aspect, drainage is accomplished by placing the biomass feedstock on a porous surface such as, for example, a cheesecloth, a piece of burlap, or a finely woven white canvas tote cloth, and allowing the liquid to drip through. In some aspects, the porous surface can be squeezed or pressed to assist in the removal of additional liquid. In another aspect, the liquid can be drained from the biomass feedstock by decantation. In one aspect, the liquid that is drained from the pretreated biomass feedstock is collected for future use. In this aspect, the liquid collected is known as a "pretreatment liquor." Pretreatment liquors contain sugars, minerals, and other nutrients that may be useful in supporting microbial growth.

In another aspect, the biomass feedstock that has been pretreated and drained can further be rinsed one or more times. In one aspect, the feedstock can be rinsed with water, with alkali solution, with acid solution, with neutral salt solution, with an organic solvent, or a combination thereof. In this aspect, the rinsate can be collected and pooled with the pretreatment liquor collected from the first drainage step.

In some aspects, before, during, or after drainage and/or rinsing, the biomass feedstock and/or pretreatment liquors can be pH adjusted to a desired value by the addition of acid and/or base. In still other aspects, once the drained liquid and/or rinsates are collected, they can be further treated to generate optimum microbial growth media. In one aspect, this further treatment can include processes such as, for example, filtration, vacuum evaporation, lyophilization, autoclave treatment, or a combination thereof. In a further aspect, additional nutrients such as sugars, amino acids, nucleotides, vitamins, salts, minerals, or combinations thereof, can further be added to the pretreatment liquors to supplement the nutrients already present. In some aspects, the microbial growth medium thus produced is used immediately after collection and preparation; in other aspects, the microbial growth medium is stored for a period of time prior to use. In one aspect, the microbes grown on the medium are fungi. In another aspect, the microbes grown on the medium are bacteria.

In yet another aspect, pretreatment liquor can be combined with enzyme production medium to enhance enzyme production.

Process Optimization

Various pretreatment protocols can be combined to optimize the processes disclosed herein. In one aspect, alkali and acid pretreatment wastes or liquors are combined to adjust solution pH to a range that will favor microbial growth and enzyme production. In a further aspect, mineral and/or organic nutrients are added to culture media and/or pretreatment wastes or liquors to enhance microbial growth and enzyme production. In an alternative aspect, acidic pretreatment mixtures, wastes, or liquors can be washed with water or dilute alkali to increase the pH of the mixtures to favor microbial growth. In one aspect, the dilute alkali can include lime, ammonium hydroxide, or a combination thereof. In another aspect, the desired pH level can be from 4.0 to 6.0. In a further aspect, the desired pH level is about 4.0, about 4.5, about 5.0, about 5.5, or about 6.0. In any of these aspects, the pH level is selected based on optimal microbial growth and enzyme production conditions.

In one aspect, starch, starchy materials, expired starchy food products, or a combination thereof, are combined with pretreated or untreated cellulosic and hemicellulosic biomass or other biomass feedstock and subjected to co-saccharification. In this aspect, the starch, starchy materials, or expired starchy food products can be selected from corn starch, potato starch, rice starch, tapioca starch, bread or other bakery products, bread waste, bakery waste, donuts, donut waste, or a combination thereof. In one aspect, the starch is used a gelatinized material, where the starch can be added to water and subsequently heated to produce gelatinized starch. In one aspect, weight ratio of starch to the biomass feedstock can be from 20:1 to 1:1, 15:1 to 1:1, 5:1 to 1:1, or about 10:1. Further in this aspect, the presence of starch in the reactor along with cellulosic and/or hemicellulosic biomass improves the overall yield of sugars in the saccharification process described herein.

In another aspect, hydrolyzed starch is combined with lignocellulosic hydrolysate and the mixture thereof is then subjected to a fermentation process. In another aspect, waste and expired products containing sugar are combined with lignocellulosic hydrolysate and subjected to a fermentation process. In either of these aspects, the presence of sugar and/or hydrolyzed starch enhances the production of fermentation products including, for example, ethanol, butanol, organic acids, and the like.

In still another aspect, metal ions can be incorporated into the fermentation mixture. In this aspect, solutions containing metal ions are added to a suspension of biomass in culture medium, water, buffer, or a combination thereof. In some aspects, enzymes or an enzyme mixture are also added to the biomass suspension. In one aspect, the metal ions are barium, cobalt, calcium, iron, potassium, manganese, zinc, or a combination thereof. In another aspect, the concentration of the one or more metal ions is 1 mM to 20 mM, 5 mM to 15 mM, 8 mM to 12 mM, or about 10 mM. In any of these aspects, the presence of metal ions enhances biomass conversion to fermentable sugars.

Enzyme Compositions

"Crude enzyme extract" as used herein is produced when certain microbial strains are grown in high-cellulose medium. "Crude enzyme extract" possesses enzymatic activity that is useful, for example, for degrading the carbohydrate linkages found in the feedstock used for biofuel production. In one aspect, "crude enzyme extract" includes other, unidentified enzymes in addition to those with known activities. In some aspects, "crude enzyme extract" is separated from microbial biomass by sand filtration or another filtration process as well as centrifugation. In one aspect, the biomass feedstock is contacted with a crude enzyme extract to convert the biomass feedstock to a saccharide.

In one aspect, crude enzyme extract is produced by microbial cells such as, for example, fungal cells suspended in a bioreactor, flask, vessel, or other container. In an alternative aspect, crude enzyme extract is produced by fungal mycelia. In yet another aspect, both individual microbial cells and fungal mycelia contribute to the production of the crude enzyme extract. In one aspect, the crude enzyme extract contains dissolved enzymes that have not been purified, separated from one another, or concentrated. In another aspect, the crude enzyme extract has been produced by a single species of microorganism.

In one aspect, the fungal strain is *Trichoderma* SG2, deposited with the American Type Culture Collection (ATCC®) and having patent deposit designation PTA-120389. *Trichoderma* SG2 was grown from a decaying switchgrass and surface soil mixture in Alabama, USA. The strain was used as-is and not subjected to mutations or genetic engineering in the laboratory. *Trichoderma* SG2 is a sporulating fungus that grows rapidly (24-48 h) on a wide range of agricultural residues using readily-available, inexpensive equipment. *Trichoderma* SG2 has the following ribosomal RNA gene sequences: intertranscribed spacer (ITS) 1 (SEQ ID NO. 1), intertranscribed spacer (ITS) 2 (SEQ ID NO. 2), and large subunit (LSU) (SEQ ID NO. 3). In another aspect, the fungal strain also includes the teleomorph of *Trichoderma* SG2, where *Hypocrea* SG2 is the sexual stage or teleomorph of *Trichoderma* SG2 while *Trichoderma* SG2 is the asexual state or anamorph.

In another aspect, the fungal strain is *Trichoderma* SG4. *Trichoderma* SG4 was grown from a decaying switchgrass and surface soil mixture in Alabama, USA. The strain was used as-is and not subjected to mutations or genetic engineering in the laboratory. *Trichoderma* SG4 has the following ribosomal RNA gene sequences: intertranscribed spacer (ITS) 1 (SEQ ID NO. 4), intertranscribed spacer (ITS) 2 (SEQ ID NO. 5), and large subunit (LSU) (SEQ ID NO. 6). In another aspect, the fungal strain also includes the teleomorph of *Trichoderma* SG4, where *Hypocrea* SG4 is the sexual stage or teleomorph of *Trichoderma* SG4 while *Trichoderma* SG4 is the asexual state or anamorph.

In another aspect, the fungal strain is *Trichoderma* FS5A. *Trichoderma* FS5A was grown from surface soil and biomass mixture in Alabama, USA. The strain was used as-is and not subjected to mutations or genetic engineering in the laboratory. *Trichoderma* FS5A has the following ribosomal RNA gene sequence: large subunit (LSU) (SEQ ID NO. 7) and intertranscribed spacer (ITS) (SEQ ID NO. 8). In another aspect, the fungal strain also includes the teleomorph of *Trichoderma* FS5A, where *Hypocrea* FS5A is the sexual stage or teleomorph of *Trichoderma* FS5A while *Trichoderma* FS5A is the asexual state or anamorph.

In another aspect, the fungal strain is *Penicillium* FS22A. *Penicillium* FS22A was grown from a compost and surface soil mixture in Alabama, USA. The strain was used as-is and not subjected to mutations or genetic engineering in the laboratory. *Penicillium* FS22A has the following ribosomal RNA gene sequence: intertranscribed spacer (ITS) (SEQ ID NO. 9).

In one aspect, the fungal strain is isolated from composite soil and/or decaying biomass. In a further aspect, the fungal strain is not genetically manipulated. In an alternative aspect, the fungal strain is genetically manipulated. In still another aspect, a mixture of genetically manipulated and non-manipulated fungal strains is used. In another aspect, the fungal strain is purchased from a type culture collection such as, for example, the American Type Culture Collection (ATCC).

In one aspect, the fungal strain is the hypercellulolytic mutant *Trichoderma reesei* RUT-C30. In this aspect, the fungal strain has been genetically manipulated and can be purchased from ATCC. In an alternative aspect, the fungal strain outperforms *Trichoderma reesei* RUT-C30 by producing higher levels of β-glucosidase and β-xylosidase activity than RUT-C30 under the same conditions. In still another aspect, *Trichoderma* SG2, *Trichoderma* SG4, *Penicillium* FS22A, or a mixture thereof, is used in conjunction with *Trichoderma reesei* RUT-C30.

In one aspect, the crude enzyme extract is produced by culturing a fungal strain such as, for example, one of those listed above, in or on a lignocellulosic medium. The lignocellulosic medium can be the same or different material as the biomass feedstock. In one aspect, the lignocellulosic medium can be an agricultural feedstock, a bioenergy grass, a forestry residue, a logging residue, a sawmill residue, animal manure, a carbohydrate waste, a recycled material, or a combination thereof. In another aspect, the lignocellulosic media is a corn cob, corn stover, wheat straw, a peanut hull, soy hull, switchgrass, gammagrass, sawdust, paper, a chemically liquefied polymer, a high sugar waste, or any combination thereof. Exemplary procedures for producing crude enzyme extracts from the fungal strains are provided in the Examples. In one aspect, the crude enzyme extract consists of supernatant and/or filtrate that has been removed from a fungal cell culture vessel or tank following fermentation to produce enzymes. In this aspect, the crude enzyme extract can be referred to as "whole cell-free culture supernatant." In a further aspect, the whole cell-free culture supernatant can be used at 100% strength or can be diluted with water, buffer, or additional culture medium to about 50% strength, about 25% strength, or about 10% strength. In still another aspect, the "whole cell-free culture supernatant" is made and incubated on the site of biofuel production. In this aspect, "whole cell-free culture supernatant" can be used to produce sugar that is converted through fermentation to ethanol, butanol, organic acids, single cell proteins, and the like.

In one aspect, the crude enzyme extract catalyzes the hydrolysis or breakdown of polysaccharides present in the biomass feedstock into oligosaccharides and/or monosaccharides. In one aspect, the polysaccharide is cellulose and/or starch and the monosaccharide is glucose. In another aspect, the polysaccharide is xylan and the monosaccharide is xylose. In a further aspect, the polysaccharide is hemicellulose and the monosaccharide is glucose, xylose, mannose, galactose, rhamnose, glucuronic acid, galacturonic acid, or a combination thereof. In yet another aspect, the polysaccharide is pectin and the monosaccharide is galacturonic acid, xylose, apiose, rhamnose, galactose, arabinose, or a combination thereof.

In one aspect, the crude enzyme extract includes cellulase, xylanase, beta-glucosidase, beta-xylosidase, or any combination thereof. In another aspect, the crude enzyme extract further includes amylase, pectinase, mannase, glucanases, laccases, oxidases, hemicellulases, and/or other plant cell-wall degrading enzymes. Not wishing to be bound by theory, the crude enzyme extract produced by *Trichoderma* SG2, *Trichoderma* SG4, *Penicillium* FS22A, or *Trichoderma* FS5A produces a mixture of enzymes and other biological components useful in the conversion of a biomass feedstock to a saccharide.

The biomass feedstock can be contacted solely with the crude enzyme extract or, the alternative, can be used with one or more other enzymes not produced from *Trichoderma* SG2, *Trichoderma* SG4, *Penicillium* FS22A, *Trichoderma* FS5A, or any combination thereof. In one aspect, the biomass feedstock is contacted with the crude enzyme extract and a second enzyme composition for hydrolyzing the biomass feedstock, where the second enzyme composition is an enzyme composition that is not produced from *Trichoderma* SG2, *Trichoderma* SG4, *Penicillium* FS22A, or *Trichoderma* FS5A.

In one aspect, the second enzyme composition can be an "artificial enzyme composition." As used herein, an "artificial enzyme composition" is any enzyme composition that involves purification of enzymes beyond simple filtration or centrifugation to remove spent biomaterial. In some aspects, an artificial enzyme composition may contain enzymes produced separately by two or more organisms and later mixed together. In some aspects, the enzymes in an artificial enzyme composition can be produced by bacteria, fungi, algae, other microorganisms, or a combination thereof. In one aspect, the microorganisms involved in producing enzymes in an artificial enzyme composition can optionally be genetically engineered to optimize enzyme production. In an additional aspect, the artificial enzyme composition can contain other compounds such as, for example, water, glycerol, solvents, salts, buffers, adjuvants, stabilizers, preservatives, and the like. In a further aspect, the microorganisms producing an artificial enzyme composition can be separated from the growth media in which they are cultured by using centrifugation or filtration. Following centrifugation or filtration, enzymes that have been secreted into the growth media can be purified by a technique such as, for example, electrophoresis, high-pressure liquid chromatography, column chromatography, affinity chromatography, isoelectric focusing, ion exchange chromatography, or any other technique for protein purification known in the art. In one aspect, following purification, the enzymes can be incorporated into artificial enzyme compositions either separately (i.e., one enzyme per artificial enzyme composition) or together (i.e., two or more enzymes per artificial enzyme composition), along with the additional compounds described above. In a further aspect, two or more artificial enzyme compositions can be mixed together to create a different artificial enzyme composition. This action can be performed at a facility such as a factory or enzyme production plant, or can be performed on-site at a farm. In yet another aspect, the artificial enzyme composition can be purchased from one or more commercial suppliers.

In one aspect, the second enzyme composition is a commercially-available enzyme. Examples of commercial enzymes useful herein include, but are not limited to, enzymes manufactured by Novozymes (e.g., Novozymes Cellic® CTec3) and Danisco (e.g., Accellerase® BG). Thus, the term a "commercial enzyme cocktail" as used herein includes (1) a mixture of one or more crude extract enzymes produced from *Trichoderma* SG2, *Trichoderma* SG4, *Penicillium* FS22A, *Trichoderma* FSSA, or any combination thereof and (2) one or more commercially-available enzymes. The relative amounts of crude enzyme extract and commercial enzyme present in the commercial enzyme cocktail can vary. In one aspect, the crude enzyme extract is from 50% to 90% by volume of the commercial enzyme cocktail, and the commercial enzyme is from 10% to 50% by volume of the commercial enzyme cocktail. In another aspect, the crude enzyme extract is from 50% to 75% by volume of the commercial enzyme cocktail, and the commercial enzyme is from 25% to 50% by volume of the commercial enzyme cocktail. In this aspect, the use of the crude enzyme extracts described herein reduces the need for the use of commercially-available enzymes, which are very expensive. Thus, the crude enzyme extracts ultimately can reduce the cost of ethanol production (e.g., lignocellulosic ethanol) from biomass feedstocks.

In one aspect, biomass feedstock can be contacted sequentially with a crude enzyme extract and a second enzyme composition (e.g., a commercial enzyme composition). In a further aspect, biomass feedstock can be contacted concurrently with a mixture of a commercial enzyme and a crude enzyme extract (i.e, a commercial enzyme cocktail). In a still further aspect, biomass feedstock can be contacted with only a crude enzyme extract.

The enzyme compositions described herein efficiently convert a biomass feedstock to a saccharide. As used herein, "saccharification" is the hydrolysis of polysaccharides or carbohydrates from feedstock to release oligosaccharides and/or monosaccharides. In some aspects, saccharification is carried out by contacting a biomass feedstock with one or more enzyme compositions. The crude enzyme extracts described above can be used alone or in combination with a second enzyme to convert a biomass feedstock to a saccharide. The crude enzyme extracts described herein are effective in the saccharification of cellulosic and/or lignocellulosic biomass feedstock followed by fermentation of the saccharified feedstock. Exemplary procedures for converting a biomass feedstock to a saccharide using the crude enzyme extracts described herein are provided in the Examples.

Prior to contacting the biomass feedstock with the enzyme compositions described herein, the biomass feedstock can be pretreated using techniques known in the art. As used herein, "pretreatment" refers to a chemical or mechanical process performed on feedstock prior to any type of fermentation process. Pretreatment can include, for example, heat or steam pretreatment, acid pretreatment, alkali pretreatment, or a combination thereof. By contrast, "virgin" feedstock is not subjected to acid, alkali, or heat pretreatment. Both "virgin" and "pretreated" feedstock may be pulverized, powdered, or milled to facilitate enzymatic processing. In one aspect, pretreatment can result in the formation of "chemically liquefied polymers," which are fermentable sugars released from biomass by mechanical or chemical processes other than enzymatic release.

In one aspect, acid pretreatment is carried out with about 2% sulfuric acid, which is dilute and non-corrosive. In another aspect, alkaline pretreatment is carried out with about 2% sodium hydroxide, which is dilute and non-corrosive. In a further aspect, the dilute acid or base can be recycled until it is saturated, resulting in significant cost savings and requiring fewer resources to be devoted to chemical waste disposal. Exemplary procedures for the pretreatment of the biomass feedstock prior to contact with the enzyme composition are provided in the Examples.

Bioreactors

The methods described herein can be performed in a batch or continuous process. In one aspect, the bioreactor can contain chambers for production of crude enzyme extract, for saccharification, and/or for alcoholic fermentation, in addition to a sand filter for separating crude enzyme extract from microbial biomass and an ice-cooled distillation column condenser for concentrating ethanol. In other aspects, the bioreactor can process multiple feedstock loads in parallel. In a further aspect, saccharification and fermentation can occur simultaneously in the same bioreactor. In one aspect, the temperature of the bioreactor is maintained at a temperature from about 30° C. to about 50° C. In a further aspect, heat is supplied to the bioreactor by burning some of the biomass feedstock or steam or heating oil to raise temperature/pressure to 121° C./15 psi for biomass feedstock pretreatment. In a still further aspect, effluents from the bioreactor can be recycled, further reducing the impact of the bioreactor on the environment.

The bioreactors useful herein can be portable such that they can be moved from site to site. In one aspect, the bioreactor is farm-deployable. In one aspect, a farm-deployable bioreactor is installed on a farm to allow local production of saccharides and ethanol for use on the farm. In another aspect, the farm-deployable bioreactor can be operated by a farm owner or farm worker and does not require extensive training to use or maintain. In some aspects, costs associated with fuel, transportation, and logistics are reduced through use of a farm-deployable bioreactor for ethanol production. In other aspects, a single farm-deployable bioreactor can be cooperatively used on a cluster of farms in the same geographical area. In a further aspect, the farm-deployable bioreactor can process feedstock collected from multiple farms. In yet another aspect, the ethanol produced by the farm-deployable bioreactor can be shared among several farms. In one aspect, a farm-deployable bioreactor is portable. In a still further aspect, use of a farm-deployable bioreactor reduces the costs of fuel ethanol production. In another aspect, reducing the cost of ethanol production results in reduced costs of downstream processes and products that make use of fuel ethanol, such as the production of biodiesel.

One embodiment of a bioreactor is depicted in schematic form in FIG. 1. The bioreactor in FIG. 1 can be portable or stationary. Referring to FIG. 1, the bioreactor has an enzymatic chamber 1 for culturing a fungal strain in the presence of a lignocellulosic medium to produce the enzyme composition. A filter 2 is in communication with the enzymatic chamber. The filter can be filled with sand or other filter media to separate the crude enzyme extract from the spent fungal strain. The filter is communication with a holding tank 3, which collects the crude enzyme extract. However, the holding tank can be an optional component. The crude enzyme extract is fed to a saccharification chamber 4 for converting biomass feedstock to saccharides. The saccharification chamber is in communication with (i) a biomass feedstock 5 or source thereof and (ii) the filter 2 (or holding tank 3). In certain embodiments, a separate line 6 for introducing a second enzyme (e.g., commercial enzyme) can be in communication with the saccharification chamber 4. In one aspect, the sand filter can be detached from the system and sterilized by, for example, autoclaving. In this aspect, the sand filter is constructed from an autoclavable material including, for example, stainless steel or autoclave-safe plastic. In another aspect, the sand filter can be sterilized in situ. In either of these aspects, sterilization of the sand filter kills any organisms present in the biomass.

The saccharides produced from the conversion of the biomass feedstock are fed to a fermentation chamber 7 for converting saccharides to ethanol. In one aspect, the saccharide is fermented in the presence of a microbial cell including bacteria, mold and yeast. In one aspect, a source of yeast 8 can be fed to the fermentation chamber. Alternatively, yeast can be added directly to the fermentation chamber. Yeast such as a *Saccharomyces* yeast, a *Pichia* yeast, or a combination thereof can be used in the fermentation chamber and process. Exemplary procedures for fermenting saccharides into ethanol are provided in the Examples.

In the case of a portable bioreactor, the enzymatic chamber, saccharification chamber, and the fermentation chamber can be present in housing 9. The housing 9 can include temperature controls for each chamber. In one aspect, the enzymatic, saccharification, and fermentation chambers are maintained at the same temperature. In another aspect, the temperatures of the enzymatic, saccharification, and fermentation chambers are independently controlled. Mixers and aerators can also be present in one or more of the chambers.

Next, the fermentation chamber is in communication with a distillation system 10. Here, ethanol vapor produced from the fermentation chamber (e.g., at a temperature of 70 to 80° C.) is introduced into the distillation system, where ethanol is isolated and collected in the ethanol collection tank 11. Distillation systems typically used in the art can be used herein.

Figure 4:
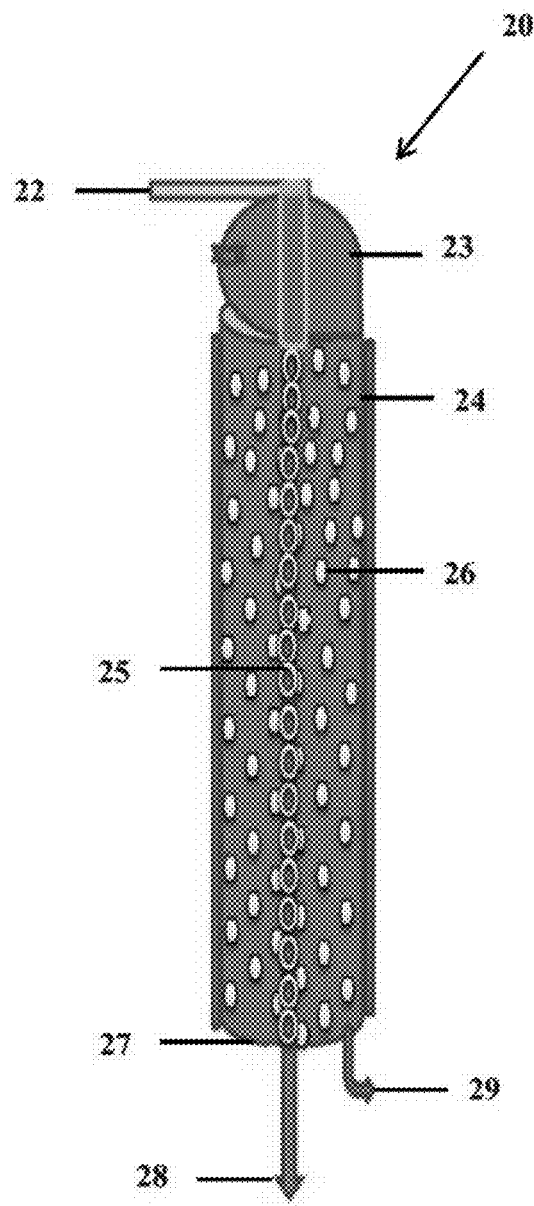
FIG. 4 shows a cross-sectional view of an example embodiment of an ice-cooled distillation column condenser.

In one aspect, the distillation condensing system 20 shown in FIG. 4 can be used herein. Ethanol vapor is introduced at the top of system 20 via inlet 22. The inlet 22 can be a fitting or tube secured to lid 23, which fits securely on top of housing 24. The lid can be fitted with a gasket or O-ring to prevent the escape of ethanol vapor from the system and to sustain cooling. A condensing coil 25 is connected to inlet 22. In certain aspects, the condensing coil and the inlet can be the same tube. For example, the condensing coil can be fed through an opening in the lid 23. The condensing coil can be made of any durable, flexible material.

The condensing coil 25 is positioned within housing 24. The housing has a sufficient diameter for receiving the condenser coil or tubing and a cooling substance 26 (e.g., ice or cooling packs). The housing can be made of any durable material such as metal, plastic (e.g., PVC), or glass. The dimensions and shape of the housing can vary depending upon the application. Referring to FIG. 4, the housing 24 is a column.

The bottom of the distillation system 20 is fitted with a second lid 27. The condensing coil 25 is connected to an outlet 28. The outlet 28 is a tube or fitting secured to lid 27, which fits securely at the bottom of housing 24. The lid 27 can also be fitted with a gasket or O-ring to prevent the escape of ethanol vapor or water from the system. In certain aspects, the condensing coil and the outlet can be the same tube. For example, the condensing coil can be fed through an opening in the lid 27. Lid 27 can also be fitted with a water outlet 29 for recovering water that has melted from the ice or condensation from cooling packs present in the housing. The water that is recovered can be re-frozen and used again in the distillation system. In other embodiments, other materials such as ice or alone or in combination with sawdust can be packed in the condenser to increase the efficiency of the condenser. While the distillation condensing system 20 is useful in the isolation of ethanol, it can be used in numerous other applications including, but not limited to, laboratory and industrial production of distilled water, and industrial and laboratory recovery of alcohols, ketones, essential oils and other volatile substances from mixtures.

Figure 5:
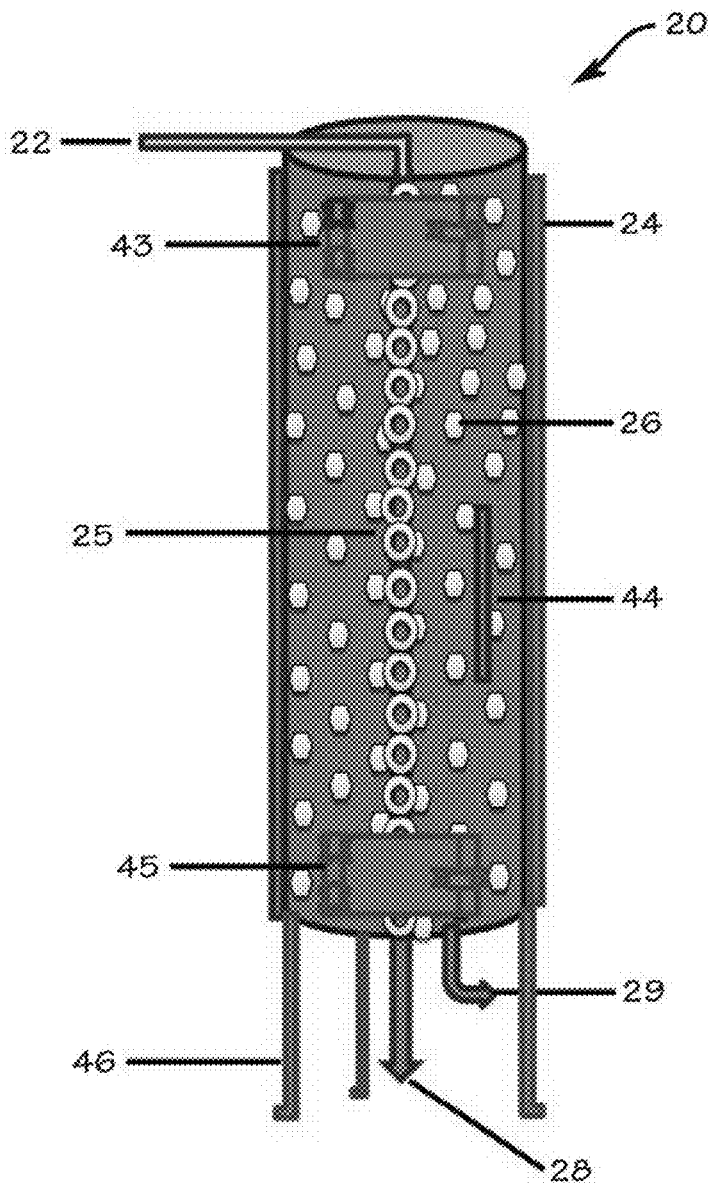
FIG. 5 shows a cross-sectional view of a second example embodiment of an ice-cooled distillation column condenser.

In some embodiments, distillation system 20 includes additional features. Referring to FIG. 5, the condenser can optionally incorporate a top side window 43 with seal, a bottom side window 45 with seal, a detachable thermometer 44, and a stand 46.

Figure 2:
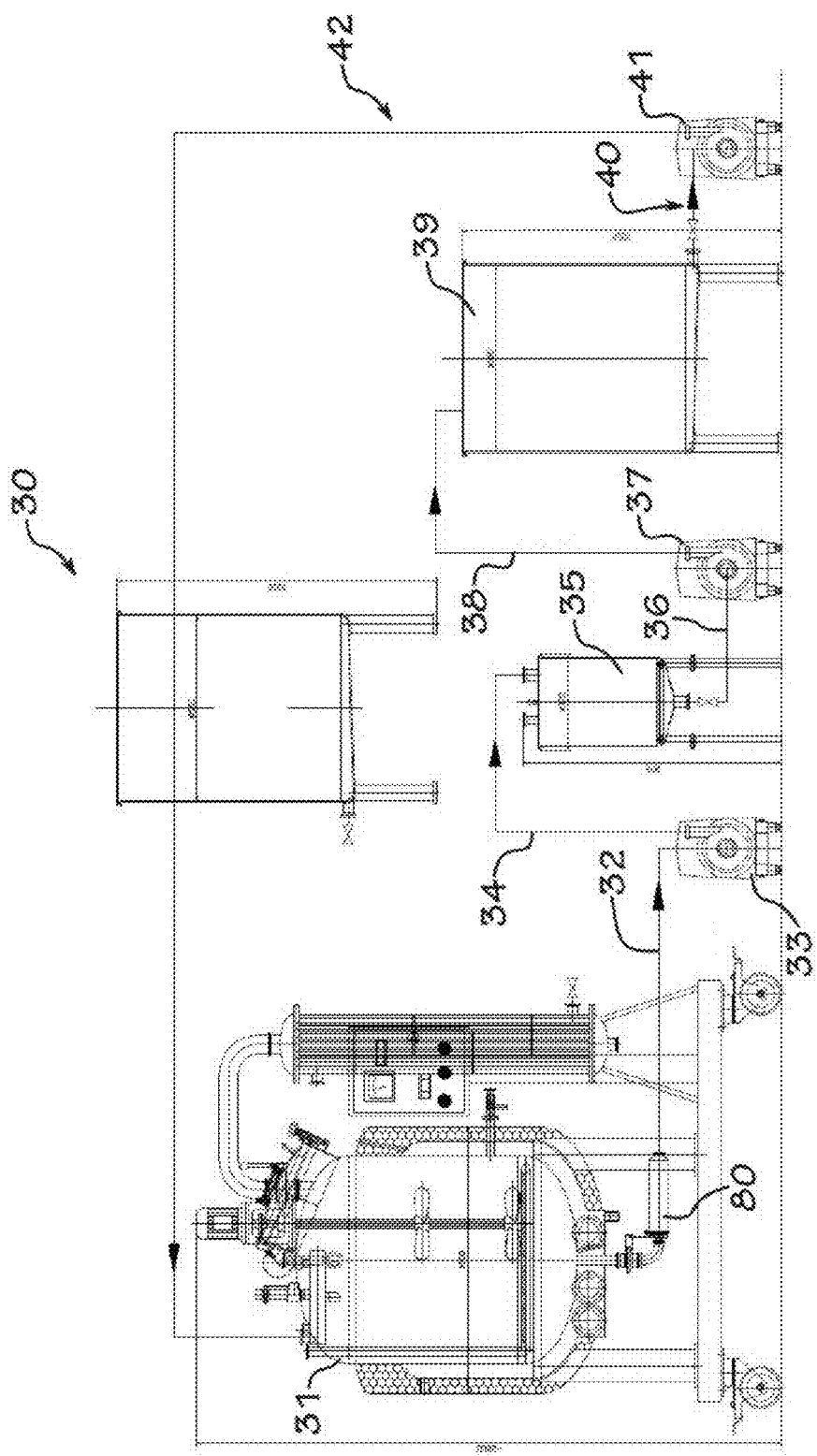
FIG. 2 shows an example embodiment of a configuration of the bioreactor system/process of the present invention, where biomass hydrolyzing enzymes can be produced and stored, where the biomass feedstock can be pretreated and solids retained in the reaction chamber, where the retained biomass feed stock can be converted to a saccharide by returning stored biomass feedstock hydrolyzing enzymes to the reaction chamber and by adding supplementary enzymes at proportions given elsewhere in this embodiment.
Figure 3:
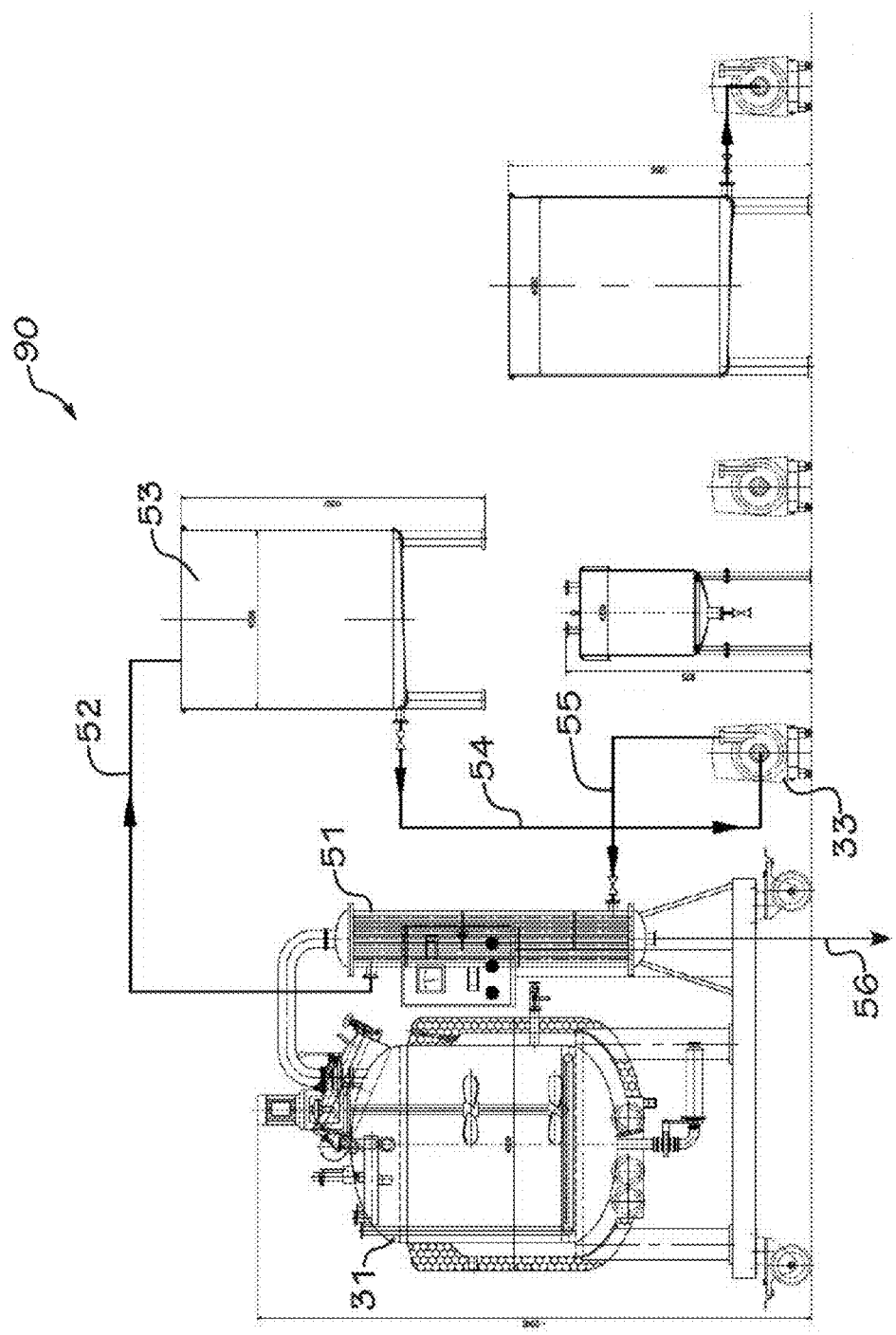
FIG. 3 shows an example embodiment of a configuration of the bioreactor system/process of the present invention, where the saccharide can be fermented in the bioreactor to produce and recover ethanol from the bioreactor by distillation.

In another aspect, the methods described herein can be performed in a single bioreactor that can perform multiple steps including enzyme production, biomass feed stock pretreatment, conversion of feed stock to saccharides, and fermentation. FIGS. 2 and 3 depict a bioreactor system/process 30 and 90, respectively, that are useful herein. Referring to FIGS. 2 and 3, bioreactor 31 can be used for enzyme production, pretreatment of biomass, saccharification, and fermentation. In one aspect, a fungal strain is cultured in the bioreactor 31 in the presence of a lignocellulosic material to produce a crude enzyme extract. Material from bioreactor 31 is passed through line 32 by pump 33, through line 34, and into sand filter 35. As the material passes through sand filter 35, spent biomass is separated from the crude enzyme extract. The crude enzyme extract is passed through line 36 by pump 37, through line 38, and into holding tank 39. From holding tank 39, the crude enzyme extract is passed through line 40 by pump 41, through line 42, and back into—bioreactor 31.

In another aspect the bioreactor 31 is employed for chemical and/or physical pretreatment of biomass feedstock, where the temperature is raised to ≥121° C. Pretreatment liqueur is then removed through a detachable filter 80 retaining pretreated biomass solids in the bioreactor 31 for subsequent conversion to saccharide by cycling back enzymes initially produced in bioreactor 31.

In another aspect, the same configuration of bioreactor system/process 30 as depicted in FIG. 2 that is used for enzyme production can be used for saccharification. In this aspect, a biomass feedstock is mixed with the crude enzyme extract and fermented in bioreactor 31 to produce a saccharide. Material from bioreactor 31 is passed through line 32 by pump 33, through line 34, and into sand filter 35. As the material passes through sand filter 35, spent biomass is separated from the saccharide. The saccharide is passed through line 36 by pump 37, through line 38, and into holding tank 39. From holding tank 39, the saccharide is passed through line 40 by pump 41, through line 42, and back into bioreactor 31.

Another embodiment of bioreactor system/process 90 is depicted in FIG. 3. In this embodiment, yeast fermentation of a saccharide is carried out in bioreactor 31. Alcohol produced during this fermentation process is vaporized and rises to the top of bioreactor 31, where it travels to condenser 51 and is condensed to liquid. The liquid alcohol passes out of condenser 51 through line 56 and is collected. During the condensation process, the coolant for condenser 51 can be recycled. In this aspect, ice water from the condenser passes out of the top of the condenser through line 52 into holding tank 53 where it can be chilled if needed. Ice water from holding tank 53 is pumped through line 54 by pump 33, through line 55, and into the bottom of condenser 51.

Figure 6:
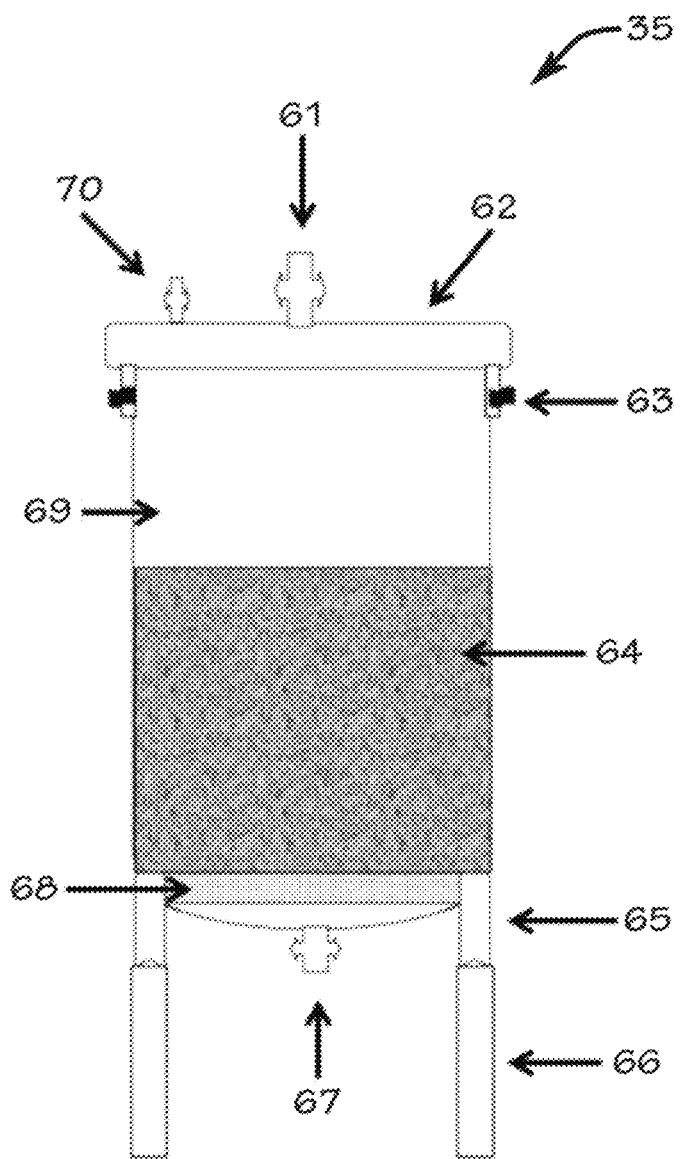
FIG. 6 shows an example embodiment of an autoclavable sand filter for biomass removal and containment.

Referring to FIG. 6, in embodiments related to enzyme production or saccharification, spent biomass can be removed from circulation in the bioreactor 30 using sand column 35. Sand column 35 includes an inlet 61 in lid 62 wherein the inlet is configured to receive biomass and enzyme mixtures or biomass and saccharides. Lid 62 may be held in place by one or more clamps 63. Sand column 35 is at least partially filled with sand 64 and includes head space 69, which can be vented to release pressure through activation of vent 70. Material passes through inlet 61 into head space 69, through sand 64, through filter bed 68, and solid matter (spent) is separated from liquid materials. The liquid materials then exit sand column 35 through outlet 67. Sand column 35 is supported by one or more detachable legs 65 and/or stand 66. The sand filter can be in-line or removable and can be made from stainless steel or autoclavable plastic.

Waste Materials and Applications Thereof

The methods described herein produce by-products that have further applications. In one aspect, the spent biomaterial from crude fungal enzyme production contains live fungal biomass along with media nutrients. Without wishing to be bound by theory, *Trichoderma* species are known to promote plant growth by degrading nutrients which the plants can then make use of, and to improve plant health by biocontrol of plant pathogens. Similarly, some *Penicillium* species are also known to promote plant health by controlling pathogenic species. In one aspect, spent biomaterial is separated from crude enzyme mixture by filtration such as, for example, through a sand column (e.g., filter 2 in FIG. 1). The spent material produced from the production of the crude enzyme extract can be stored in a tank or vessel for future use (12 in FIG. 1).

In another aspect, spent biomaterial is any solid biomass remaining after fermentation to produce ethanol. For example, the spent biomaterial can include, for example, yeast biomass remaining after alcoholic fermentation.

In some aspects, the spent biomaterial can be used, for example, as an ingredient in animal feed, as a source from which nutrients such as amino acids can be extracted, or in soil remediation applications. In one aspect, spent biomaterial can contain living and/or dead fungal cells and/or fungal mycelia, incompletely processed biomass feedstock, any other solid material remaining after filtration or distillation, or a combination thereof.

The spent biomaterial contains nutrients that can be used for soil remediation. Further, the spent biomaterial from any step in the methods and processes disclosed herein can be used for animal feed or feed for aquatic organisms. Spent biomaterial contains, for example, partially hydrolyzed cellulosic feedstock and yeast biomass which can be used (i) to make feed blends, (ii) as a substrate to produce "value-added" feed materials, and (iii) as a source for extracted nutrients such as amino acids.

Throughout this application, where publications are referenced, the disclosures of these publications in their entireties are hereby incorporated by reference into this application in order to more fully describe the state of the art to which this invention pertains.

EXAMPLES

The following examples are put forth so as to provide those of ordinary skill in the art with a complete disclosure and description of how the compositions and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.), but some errors and deviations should be accounted for. Unless indicated otherwise, parts are parts by weight, temperature is in ° C. or is at ambient temperature, and pressure is at or near atmospheric. Numerous variations and combinations of reaction conditions, e.g. component concentrations, desired solvents, solvent mixtures, temperatures, pressures, and other reaction ranges and conditions can be used to optimize the product purity and yield obtained from the described process. Only reasonable and routine experimentation will be required to optimize such process conditions.

Example 1: Preparation of Crude Fungal Extract

A crude enzyme extract was prepared using fermentation processes. Fungal strains tested included *Trichoderma* SG2, SG4, and FS5A and *Penicillium* FS22A.

Inocula were prepared by introducing loops full of fungal cells from slants into 50 mL of sterile, high-solids medium (5% all-purpose flour, 0.1% yeast extract, and 0.1% peptone) in 250 mL flasks and were incubated at 30° C. for 72 h with shaking at 200 rpm.

Crude enzyme production was carried out in ten 250 mL flasks containing an optimized screening medium. (One liter of medium comprised 6.2 g powdered waste paper, 9.6 g pulverized switch grass, 1.4 g peptone, 0.6 g yeast extract, 0.5 g polysorbate 80, 2 g $KH_2PO_4$, 1.2 g $(NH_4)_2SO_4$, 0.5 g $MgSO_4 \cdot 7H_2O$, 0.1 g $CaCl_2$, 0.003 g $FeSO_4 \cdot 7H_2O$, and 2 mL Fotch mineral element solution. The pH varied from 5.2 to 5.35 and was not further modified.) Each flask contained 50 mL of medium and flasks were sterilized at 121° C. for 1 h before inoculation. 10% of the 72 h inoculum was added into each flask aseptically; flasks were incubated at 30° C. for 5 days. The crude enzyme samples obtained on days 2, 4, and 5 were assayed for cellulase, xylanase, β-glucosidase, and β-xylosidase activities. On the fifth day of enzyme production, broth was transferred into sterile 50 mL centrifuge tubes and centrifuged at 5,000 rpm for 10 min. Supernatants were used for biomass saccharification.

End-of-fermentation samples were analyzed for cellulase, xylanase, β-glucosidase, and β-xylosidase activities. Filter paper discs were used for the cellulase assay. 10 discs were placed in glass test tubes and 0.5 mL of 100 mM sodium acetate buffer (pH 5.0) was added. 0.5 mL of end-of-fermentation sample (crude enzyme extract) was further added. Tubes were incubated at 50° C. for 30 min. Enzyme reactions were stopped with 3,5-dinitrosalicylic acid (DNS reagent) and 40% sodium potassium tartrate. Sample mixtures were placed in a boiling water bath for 10 min and cooled to room temperature. Using a spectrophotometer, optical density (OD) was read at 575 nm, and concentration of reducing sugar released in mg/mL was calculated using a standard glucose curve. The same procedure was followed for the xylanase assay except that the substrate was oat xylan rather than filter paper.

For β-glucosidase and β-xylosidase, the substrates p-nitrophenyl β-D-glucoside and p-nitrophenyl β-D-xyloside were used, respectively. In brief, approximately 800 μL of 100 mM sodium acetate buffer (pH 5.0) was added to 100 mL of 40 mM substrate for β-glucosidase and 20 mM substrate for β-xylosidase, 100 μL of crude enzyme extract was added, incubated at 50° C. for 30 min, and immediately transferred into an ice-cold water bath. The enzyme reaction was stopped using 1 mL of chilled $Na_2CO_3$. Sample OD was read at 405 nm and enzyme activity calculated as micromoles of p-nitrophenol released per mL of enzyme extract using a standard curve.

The enzyme activities (U/mL/30 min) of unconcentrated culture filtrates from *Trichoderma* SG2 were cellulase: 11.3, xylanase: 108.61, β-glucosidase: 16.75, and β-xylosidase: 13.45. The enzyme activities of *Trichoderma* SG4, *Penicillium* FS22A, and *Trichoderma* FS5A are provided in Table 1.

TABLE 1

Crude Enzyme Activities of *Trichoderma* SG4, *Trichoderma* FS5A, and *Penicillium* FS22A

| Fungal Strain | Incubation Time (Days) | Cellulase Activity (U/mL/30 min) | Xylanase Activity (U/mL/30 min) | β-Glucosidase Activity (U/mL/30 min) | β-Xylosidase Activity (U/mL/30 min) |
|---|---|---|---|---|---|
| SG4 | 2 | 6.33 ± 0.14 | 36.76 ± 0.28 | 4.47 ± 0.01 | 0.81 ± 0.01 |
|  | 4 | 7.54 ± 0.03 | 38.25 ± 0.03 | 7.17 ± 0.04 | 5.96 ± 0.11 |
|  | 5 | 10.51 ± 0.45 | 48.99 ± 2.31 | 24.97 ± 2.82 | 7.47 ± 0.41 |
| FS5A | 2 | 5.97 ± 0.06 | 44.31 ± 0.28 | 1.68 ± 0.01 | 4.62 ± 0.05 |
|  | 4 | 6.38 ± 0 | 38.91 ± 0.06 | 2.45 ± 0.02 | 6.95 ± 0.02 |
|  | 5 | 7.56 ± 0.49 | 44.23 ± 0.89 | 5.77 ± 0.39 | 1.85 ± 0.01 |
| FS22A | 2 | 1.76 ± 0.01 | 37.24 ± 0.23 | 0.29 ± 0 | 0.17 ± 0 |
|  | 4 | 7.92 ± 0.04 | 45.98 ± 0.16 | 1.26 ± 0.04 | 1.67 ± 0.01 |
|  | 5 | 11.68 ± 1.04 | 47.79 ± 0.97 | 0.94 ± 0.13 | 2.51 ± 0.34 |

By comparison, the activities of commercial enzymes (normally concentrated and stabilized culture filtrate) were cellulase (Novozymes NS22086): 31.46, xylanase (Novozymes NS22083): 55.21, and β-glucosidase (Novozymes NS22118): 24.72. Levels of sugar release from switchgrass by the crude enzyme extracts of SG4, FS5A, and FS22A are provided in Table 2.

TABLE 2

Saccharification of 2% Switchgrass by Crude Enzyme Extracts

| Fungal Strain | Incubation Time (Hours) | Glucose Release (g/L) | Xylose Release (g/L) |
|---|---|---|---|
| SG4 | 24 | 1.18 ± 0.02 | 0.54 ± 0.02 |
|  | 48 | 1.39 ± 0 | 0.69 ± 0.04 |
|  | 72 | 1.51 ± 0 | 0.95 ± 0 |
| FS5A | 24 | 0.77 ± 0.02 | 0.28 ± 0.02 |
|  | 48 | 0.98 ± 0.03 | 0.25 ± 0.02 |
|  | 72 | 1.31 ± 0.05 | 0.41 ± 0.02 |
| FS22A | 24 | 2.14 ± 0.02 | 0.60 ± 0.02 |
|  | 48 | 3.04 ± 0.05 | 0.89 ± 0.04 |
|  | 72 | 3.46 ± 0.08 | 1.22 ± 0.10 |

Example 2: Evaluation of Pretreatment Protocols

Pretreatment of switchgrass and the effect of pretreatment on saccharification by *Trichoderma* SG2 enzymes in combination with a commercial enzyme cocktail were examined Virgin switchgrass did not receive any pretreatment.

Heat pretreatment was carried out by autoclaving 2% switchgrass at 121° C. for 1 h. After autoclaving, samples were allowed to cool to room temperature and liquid was drained using a finely woven white canvas tote cloth.

Acid pretreatment was carried out using 2% sulfuric acid. 100 g of switchgrass was soaked in 2% sulfuric acid and autoclaved at 121° C. for 1 h. After autoclaving, samples were allowed to cool to room temperature, liquid was drained using a finely woven white canvas tote cloth and the acid-pretreated switchgrass was washed several times with water to completely remove any remaining acid. After 4-5 washes, the pH of the wash liquid was tested. Samples were further washed if the pH was less than 5. Washed switchgrass was dried at room temperature for 72 h and stored in airtight zip-top plastic bags until further use.

Alkali pretreatment was carried out using 2% sodium hydroxide. 100 g of switchgrass was soaked in 2% sodium hydroxide solution and autoclaved at 121° C. for 1 h. After autoclaving, samples were allowed to cool to room temperature, liquid was drained using a finely woven white canvas tote cloth and the alkali-pretreated switchgrass was washed several times to completely remove any remaining base. After 4-5 washes, the pH of the wash liquid was tested. Samples were further washed if the pH was greater than 7. Washed switchgrass was dried at room temperature for 72 h and stored in airtight zip-top plastic bags until further use.

*Trichoderma* SG2 crude enzyme extract was produced and enzyme activities were assayed according to Example 1. Saccharification of pretreated samples was carried out in 100 mL flasks with airtight caps; all experiments were performed in duplicate. 10 mL of crude enzyme reaction mixture was added to each flask. Approximately 2% switchgrass (virgin, autoclaved, acid-pretreated, or alkali-pretreated) was added to the flasks. Novozymes enzymes NS22086 (cellulase), NS22083 (xylanase), NS22118 (β-glucosidase), and NS22002 (hemicellulase) were used in the commercial enzyme cocktail. Commercial enzyme dosage was administered according to the manufacturer's instructions (5% cellulase, 0.25% xylanase, 0.6% β-glucosidase, and 2% hemicellulase for a total of 7.85% commercial enzyme preparation per % total biomass feedstock solids), or was proportionally decreased to 50% or to 25% of the recommended concentration (3.93% enzymes or 1.96% enzymes per % total biomass feedstock solids, respectively).

Enzyme treatments included crude aqueous extract of *Trichoderma* SG2 culture (C), commercial enzymes at the recommended dosage (N), crude aqueous extract of *Trichoderma* SG2 supplemented with 50% of the recommended Novozymes enzyme dosage (C50N), and crude aqueous extract of *Trichoderma* SG2 supplemented with 25% of the recommended Novozymes enzyme dosage (C25N). Saccharification was carried out at 50° C. at 80 rpm mixing using a Thermo Scientific MaxQ 4000 shaker. All flasks were closed tightly to prevent the escape of moisture. 0.5 mL of sample was drawn at 24 h intervals up to 72 h. Sugars in each sample were quantified using HPLC according to a published method. Shimadzu HPLC equipped with RID detector and Lab solution software was used for determining levels of glucose and ethanol. For separation, Phenomenex Rezex-ROA organic acid column cross-linked with 8% hydrogen resin was used. Column oven temperature was adjusted to 82° C. HPLC-grade water was used as the mobile phase with a flow rate of 0.6 mL/min.

Results from the saccharification of switchgrass after different pretreatment schemes are presented in Tables 3-6.

TABLE 3

Saccharification of 2% Virgin Switchgrass

| Treatment | Incubation Time (Hours) | Glucose Production (g/L) | Xylose Production (g/L) |
|---|---|---|---|
| C | 24 | 0.12 ± 0.02 | 0.09 ± 0.02 |
|  | 48 | 0.16 ± 0 | 0 ± 0 |
|  | 72 | 0.14 ± 0.01 | 0 ± 0 |
| N | 24 | 1.61 ± 0.03 | 0.60 ± 0.01 |
|  | 48 | 1.87 ± 0.07 | 0.74 ± 0.04 |
|  | 72 | 1.97 ± 0.06 | 0.79 ± 0.03 |
| C50N | 24 | 0.13 ± 0.01 | 0.58 ± 0.11 |
|  | 48 | 0.16 ± 0.01 | 0.19 ± 0.08 |
|  | 72 | 0.15 ± 0 | 0 ± 0 |
| C25N | 24 | 0.77 ± 0.05 | 0.51 ± 0.03 |
|  | 48 | 0.16 ± 0 | 0.33 ± 0.03 |
|  | 72 | 0.14 ± 0.01 | 0 ± 0 |

TABLE 4

Saccharification of 2% Heat Pretreated Switchgrass

| Treatment | Incubation Time (Hours) | Glucose Production (g/L) | Xylose Production (g/L) |
|---|---|---|---|
| C | 24 | 0.52 ± 0.01 | 0.28 ± 0 |
|  | 48 | 0.61 ± 0.01 | 0.33 ± 0 |
|  | 72 | 0.63 ± 0.02 | 0.33 ± 0 |
| N | 24 | 2.11 ± 0.05 | 0.78 ± 0.02 |
|  | 48 | 2.39 ± 0.13 | 0.89 ± 0.05 |
|  | 72 | 2.51 ± 0.11 | 1.00 ± 0.04 |
| C50N | 24 | 1.67 ± 0.14 | 0.67 ± 0.05 |
|  | 48 | 1.99 ± 0.16 | 0.85 ± 0.05 |
|  | 72 | 2.18 ± 0.15 | 1.03 ± 0.04 |
| C25N | 24 | 1.32 ± 0.19 | 0.60 ± 0.07 |
|  | 48 | 1.58 ± 0.28 | 0.77 ± 0.11 |
|  | 72 | 1.77 ± 0.27 | 0.94 ± 0.11 |

TABLE 5

Saccharification of 2% Alkali Pretreated Switchgrass

| Treatment | Incubation Time (Hours) | Glucose Production (g/L) | Xylose Production (g/L) |
|---|---|---|---|
| C    | 24 | 1.48 ± 0.08 | 0.99 ± 0.05 |
|      | 48 | 1.59 ± 0.07 | 1.19 ± 0.03 |
|      | 72 | 1.49 ± 0.10 | 1.31 ± 0.03 |
| N    | 24 | 0.40 ± 0.21 | 1.23 ± 0.31 |
|      | 48 | 0.13 ± 0.01 | 2.15 ± 0.10 |
|      | 72 | 0.16 ± 0.01 | 2.32 ± 0.11 |
| C50N | 24 | 9.06 ± 0.68 | 2.91 ± 0.10 |
|      | 48 | 0.22 ± 0    | 3.78 ± 0.13 |
|      | 72 | 0.14 ± 0    | 3.30 ± 0.13 |
| C25N | 24 | 6.75 ± 0.08 | 1.85 ± 0.01 |
|      | 48 | 0.38 ± 0.03 | 2.78 ± 0.16 |
|      | 72 | 0.22 ± 0.02 | 3.38 ± 0.16 |

TABLE 6

Saccharification of 2% Acid Pretreated Switchgrass

| Treatment | Incubation Time (Hours) | Glucose Production (g/L) | Xylose Production (g/L) |
|---|---|---|---|
| C    | 24 | 3.34 ± 0.02 | 0.82 ± 0.02 |
|      | 48 | 3.69 ± 0.02 | 0.94 ± 0.02 |
|      | 72 | 3.77 ± 0.03 | 0.95 ± 0.03 |
| N    | 24 | 3.77 ± 0    | 0.78 ± 0    |
|      | 48 | 4.17 ± 0.01 | 0.89 ± 0.01 |
|      | 72 | 4.32 ± 0.06 | 1.19 ± 0.06 |
| C50N | 24 | 4.86 ± 0.05 | 1.07 ± 0.05 |
|      | 48 | 5.60 ± 0.09 | 1.31 ± 0.09 |
|      | 72 | 5.61 ± 0.02 | 1.64 ± 0.02 |
| C25N | 24 | 4.48 ± 0.07 | 1.02 ± 0.07 |
|      | 48 | 4.96 ± 0.06 | 1.37 ± 0.06 |
|      | 72 | 5.11 ± 0.04 | 1.26 ± 0.04 |

Ethanol fermentation was carried out on 72 h-saccharified samples. 100 µL of 48 h *Saccharomyces cerevisiae* inoculum was added and the flasks were incubated at 30° C. with mixing at 65 rpm. Samples were drawn from flasks at 24 h intervals up to 72 h to quantify ethanol production. Ethanol production was only observed in acid-pretreated switchgrass samples (Table 7).

TABLE 7

Ethanol Production from Saccharified Acid-Pretreated Switchgrass

| Treatment | Ethanol (g/L) |
|---|---|
| C    | 1.01 ± 0.10 |
| N    | 1.23 ± 0.01 |
| C50N | 2.12 ± 0.06 |
| C25N | 1.70 ± 0.15 |

Example 3: Evaluation of Feedstock Materials

In this Example, saccharification of three different acid-pretreated feedstocks by crude enzyme extracts of *Trichoderma* SG2 and *Penicillium* FS22A and/or by commercial enzyme cocktails is examined.

Acid-pretreatment of switchgrass, gammagrass, and sawdust was performed according to the method of Example 2.

Moisture determination of virgin and pretreated biomass was carried out using a Mettler-Toledo moisture meter (HB 43-5 Halogen). 1 g of sample (pretreated or control) was placed in the aluminum pan of the moisture meter and moisture content was recorded in % following a preloaded method in the instrument. At least two readings were recorded for each sample. Moisture contents of various types of virgin and acid-pretreated biomass are provided in Table 8.

TABLE 8

Moisture Content in Virgin and Acid-Pretreated Biomass

| Biomass | Moisture Content (%) | |
|---|---|---|
|  | Virgin | Acid-Pretreated |
| Gammagrass  | 7.61 ± 0.20  | 8.4 ± 0.02  |
| Sawdust     | 14.43 ± 0.38 | 10.9 ± 0.43 |
| Switchgrass | 8.71 ± 0.13  | 8.83 ± 0.01 |

Crude enzyme extracts of *Trichoderma* SG2 and *Penicillium* FS22A were produced as described in Example 1; enzyme activities for these extracts are provided in Table 9.

TABLE 9

Crude Enzyme Activities of *Trichoderma* SG2 and *Penicillium* FS22A

| Fungal Strain | Cellulase Activity (U/mL/30 min) | Xylanase Activity (U/mL/30 min) | β-Glucosidase Activity (U/mL/30 min) | β-Xylosidase Activity (U/mL/30 min) |
|---|---|---|---|---|
| SG2   | 20.57 ± 0.002 | 64.6 ± 0.009  | 17.66 ± 0.009 | 25.84 ± 0.013 |
| FS22A | 19.18 ± 0.008 | 56.98 ± 0.045 | 17.54 ± 0.002 | 5.57 ± 0.017 |

Enzyme treatments were as follows: C was crude aqueous extract of SG2 or FS22A culture, C25N was crude extract combined with a commercial enzyme cocktail at 25% strength, C50N was crude extract combined with a commercial enzyme cocktail at 50% strength, N25 was a commercial enzyme cocktail at 25% strength, and N50 was a commercial enzyme cocktail at 50% strength. Saccharification, sugar quantification, and ethanol fermentation were performed as described in Example 2.

Overall analysis of the saccharification by *Penicillium* FS22A of the three types of biomass tested revealed that switchgrass yielded the highest glucose level, followed by gammagrass and, lastly, sawdust. Further, with all three types of biomass, the highest saccharification resulted from the C50N treatment; saccharification after 72 h resulted in the numerically highest sugar yield. Sugar release for each type of biomass feedstock at various time points is provided in Tables 10-12.

TABLE 10

Saccharification of 2% Gammagrass by *Penicillium* FS22A Crude Enzyme Extract

| Treatment | Incubation Time (Hours) | Glucose Production (g/L) | Xylose Production (g/L) |
|---|---|---|---|
| C    | 24 | 1.83 ± 0.005 | 0.57 ± 0.005 |
|      | 48 | 2.3 ± 0.005  | 0.6 ± 0      |
|      | 72 | 2.5 ± 0      | 0.65 ± 0.005 |
| C25N | 24 | 1.79 ± 0     | 0.59 ± 0     |
|      | 48 | 1.9 ± 0      | 0.61 ± 0     |
|      | 72 | 1.9 ± 0.070  | 0.76 ± 0.250 |

TABLE 10-continued

Saccharification of 2% Gammagrass by *Penicillium* FS22A Crude Enzyme Extract

| Treatment | Incubation Time (Hours) | Glucose Production (g/L) | Xylose Production (g/L) |
|---|---|---|---|
| C50N | 24 | 2.35 ± 0.005 | 0.75 ± 0 |
|  | 48 | 2.58 ± 0 | 0.75 ± 0 |
|  | 72 | 2.63 ± 0 | 0.78 ± 0.005 |
| N | 24 | 2.04 ± 0 | 0.31 ± 0 |
|  | 48 | 2.18 ± 0 | 0.34 ± 0 |
|  | 72 | 2.27 ± 0 | 0.37 ± 0 |
| N25 | 24 | 0.76 ± 0 | 0.19 ± 0 |
|  | 48 | 0.77 ± 0 | 0.21 ± .000 |
|  | 72 | 0.8 ± 0 | 0.23 ± 0 |
| N50 | 24 | 1.42 ± 0 | 0.245 ± 0.005 |
|  | 48 | 1.48 ± 0 | 0.27 ± 0 |
|  | 72 | 1.525 ± 0.005 | 1.635 ± 1.340 |

TABLE 11

Saccharification of 2% Sawdust by *Penicillium* FS22A Crude Enzyme Extract

| Treatment | Incubation Time (Hours) | Glucose Production (g/L) | Xylose Production (g/L) |
|---|---|---|---|
| C | 24 | 0.82 ± 0 | 0.3 ± 0 |
|  | 48 | 1.08 ± 0 | 0.35 ± 0 |
|  | 72 | 1.16 ± 0 | 0.37 ± 0 |
| C25N | 24 | 1.11 ± 0 | 0.31 ± 0 |
|  | 48 | 1.4 ± 0 | 0.35 ± 0 |
|  | 72 | 1.35 ± 0 | 0.35 ± 0 |
| C50N | 24 | 1.61 ± 0 | 0.5 ± 0 |
|  | 48 | 1.76 ± 0.005 | 0.4 ± 0 |
|  | 72 | 1.83 ± 0.005 | 0.3 ± 0.130 |
| N | 24 | 0.61 ± 0 | 0.1 ± 0 |
|  | 48 | 0.66 ± 0.005 | 0.11 ± 0 |
|  | 72 | 0.68 ± 0 | 0.12 ± 0.005 |
| N25 | 24 | 0.05 ± 0 | 0.05 ± 0 |
|  | 48 | 0.18 ± 0 | 0.05 ± 0 |
|  | 72 | 0.68 ± 0 | 0.12 ± 0.005 |
| N50 | 24 | 0.36 ± 0 | 0.07 ± 0 |
|  | 48 | 0.37 ± 0 | 0.08 ± 0 |
|  | 72 | 0.19 ± 0 | 0.07 ± 0.005 |

TABLE 12

Saccharification of 2% Switchgrass by *Penicillium* FS22A Crude Enzyme Extract

| Treatment | Incubation Time (Hours) | Glucose Production (g/L) | Xylose Production (g/L) |
|---|---|---|---|
| C | 24 | 0.39 ± 0.005 | 0.1 ± 0.005 |
|  | 48 | 3.02 ± 0 | 0.65 ± 0 |
|  | 72 | 4.41 ± 0.35 | 1.03 ± 0.05 |
| C25N | 24 | 2.77 ± 0.24 | 0.65 ± 0.04 |
|  | 48 | 3.95 ± 0.39 | 0.97 ± 0.06 |
|  | 72 | 5.77 ± 0.5 | 1.24 ± 0.05 |
| C50N | 24 | 4 ± 0.02 | 0.84 ± 0.02 |
|  | 48 | 6 ± 0.26 | 1.75 ± 0.035 |
|  | 72 | 7.13 ± 0.32 | 1.83 ± 0.06 |
| N | 24 | 6.38 ± 0.19 | 1.27 ± 0.16 |
|  | 48 | 3.77 ± 0 | 0.8 ± 0 |
|  | 72 | 4.06 ± 0 | 0.89 ± 0.005 |
| N25 | 24 | 3.57 ± 0.02 | 0.73 ± 0 |
|  | 48 | 21 ± 0 | 0.6 ± 0 |
|  | 72 | 2.19 ± 0 | 0.66 ± 0 |
| N50 | 24 | 2 ± 0.005 | 0.55 ± 0 |
|  | 48 | 3.16 ± 0 | 0.72 ± 0 |
|  | 72 | 3.32 ± 0.01 | 0.87 ± 0.05 |

Overall analysis of the saccharification by *Trichoderma* SG2 of the three types of biomass tested revealed that switchgrass yielded the highest glucose level, followed by gammagrass and, lastly, sawdust. Further, with all three types of biomass, the highest saccharification resulted from the C50N and/or C25N treatments, with saccharification after 72 h generally producing the numerically highest sugar yields. Sugar release for each type of biomass feedstock at various time points is provided in Tables 13-15.

TABLE 13

Saccharification of 2% Gammagrass by *Trichoderma* SG2 Crude Enzyme Extract

| Treatment | Incubation Time (Hours) | Glucose Production (g/L) | Xylose Production (g/L) |
|---|---|---|---|
| C | 24 | 2.53 ± 0 | 0.42 ± 0 |
|  | 48 | 2.7 ± 0.005 | 0.45 ± 0 |
|  | 72 | 2.8 ± 0 | 0.27 ± 0.22 |
| C25N | 24 | 3.43 ± 0.005 | 0.56 ± 0 |
|  | 48 | 3.57 ± 0 | 0.75 ± 0 |
|  | 72 | 3.68 ± 0 | 0.83 ± 0.005 |
| C50N | 24 | 3.83 ± 0.005 | 0.61 ± 0 |
|  | 48 | 3.97 ± 0 | 0.66 ± 0 |
|  | 72 | 4.19 ± 0.005 | 0.7 ± 0.01 |
| N | 24 | 2.04 ± 0 | 0.31 ± 0 |
|  | 48 | 2.18 ± 0 | 0.34 ± 0 |
|  | 72 | 2.27 ± 0 | 0.37 ± 0 |
| N25 | 24 | 0.76 ± 0 | 0.19 ± 0 |
|  | 48 | 0.77 ± 0 | 0.21 ± 0 |
|  | 72 | 0.8 ± 0 | 0.23 ± 0 |
| N50 | 24 | 1.42 ± 0 | 0.245 ± 0.005 |
|  | 48 | 1.48 ± 0 | 0.27 ± 0 |
|  | 72 | 1.525 ± 0.005 | 1.635 ± 1.34 |

TABLE 14

Saccharification of 2% Sawdust by *Trichoderma* SG2 Crude Enzyme Extract

| Treatment | Incubation Time (Hours) | Glucose Production (g/L) | Xylose Production (g/L) |
|---|---|---|---|
| C | 24 | 1.02 ± 0 | 0.32 ± 0.005 |
|  | 48 | 1.11 ± 0 | 0.35 ± 0 |
|  | 72 | 1.2 ± 0.005 | 0.37 ± 0 |
| C25N | 24 | 0.94 ± 0.02 | 0.23 ± 0.02 |
|  | 48 | 1.03 ± 0.005 | 0.37 ± 0 |
|  | 72 | 1.1 ± 0 | 0.4 ± 0.005 |
| C50N | 24 | 1.2 ± 0.005 | 0.27 ± 0.005 |
|  | 48 | 1.29 ± 0.005 | 0.44 ± 0 |
|  | 72 | 1.4 ± 0.005 | 0.47 ± 0 |
| N | 24 | 0.61 ± 0 | 0.1 ± 0 |
|  | 48 | 0.66 ± 0.005 | 0.11 ± 0 |
|  | 72 | 0.68 ± 0 | 0.12 ± 0.005 |
| N25 | 24 | 0.05 ± 0 | 0.05 ± 0 |
|  | 48 | 0.18 ± 0 | 0.05 ± 0 |
|  | 72 | 0.68 ± 0 | 0.12 ± 0.005 |
| N50 | 24 | 0.36 ± 0 | 0.07 ± 0 |
|  | 48 | 0.37 ± 0 | 0.08 ± 0 |
|  | 72 | 0.19 ± 0 | 0.07 ± 0.005 |

TABLE 15

Saccharification of 2% Switchgrass by *Trichoderma* SG2 Crude Enzyme Extract

| Treatment | Incubation Time (Hours) | Glucose Production (g/L) | Xylose Production (g/L) |
|---|---|---|---|
| C | 24 | 2.83 ± 0.06 | 0.79 ± 0.06 |
|  | 48 | 2.9 ± 0.01 | 0.78 ± 0.005 |
|  | 72 | 2.99 ± 0 | 0.82 ± 0 |

TABLE 15-continued

Saccharification of 2% Switchgrass by *Trichoderma* SG2 Crude Enzyme Extract

| Treatment | Incubation Time (Hours) | Glucose Production (g/L) | Xylose Production (g/L) |
|---|---|---|---|
| C25N | 24 | 4.8 ± 0.01 | 1.2 ± 0 |
|  | 48 | 5.2 ± 0.005 | 1.3 ± 0 |
|  | 72 | 5.35 ± 0 | 1.36 ± 0 |
| C50N | 24 | 4.68 ± 0 | 1.2 ± 0.005 |
|  | 48 | 4.9 ± 0.005 | 1.2 ± 0.005 |
|  | 72 | 5.26 ± 0.01 | 1.41 ± 0.01 |
| N | 24 | 3.38 ± 0.19 | 1.27 ± 0.16 |
|  | 48 | 3.77 ± 0 | 0.8 ± 0 |
|  | 72 | 4.06 ± 0 | 0.89 ± 0.005 |
| N25 | 24 | 3.57 ± 0.02 | 0.73 ± 0 |
|  | 48 | 2.1 ± 0 | 0.6 ± 0 |
|  | 72 | 2.19 ± 0 | 0.66 ± 0 |
| N50 | 24 | 2 ± 0.005 | 0.55 ± 0 |
|  | 48 | 3.16 ± 0 | 0.72 ± 0 |
|  | 72 | 3.32 ± 0.01 | 0.87 ± 0.05 |

Ethanol yield of SG2 saccharified substrates was statistically significant after 24 h of yeast fermentation. Ethanol yields (in g/L) for each enzyme treatment are presented in Table 16 for a crude enzyme cocktail from *Trichoderma* SG2; biomass was saccharified for 72 h prior to yeast fermentation.

TABLE 16

Ethanol Fermentation of SG2 Saccharified Feedstock Biomass

| Treatment | Feedstock | Residual Glucose (g/L) | Residual Xylose (g/L) | Ethanol (g/L) |
|---|---|---|---|---|
| C | Gammagrass | 0 ± 0 | 0.43 ± 0 | 0 ± 0 |
|  | Sawdust | 0 ± 0 | 0.3 ± 0 | 0 ± 0 |
|  | Switchgrass | 0.15 ± 0 | 0.74 ± 0 | 0 ± 0 |
| C25N | Gammagrass | 0 ± 0 | 0.68 ± 0 | 0 ± 0 |
|  | Sawdust | 0 ± 0 | 0.22 ± 0.005 | 0 ± 0 |
|  | Switchgrass | 0.11 ± 0 | 1.15 ± 0 | 0.14 ± 0.005 |
| C50N | Gammagrass | 0 ± 0 | 0.59 ± 0 | 0 ± 0 |
|  | Sawdust | 0 ± 0 | 0.23 ± 0 | 0 ± 0 |
|  | Switchgrass | 0.13 ± 0 | 1.21 ± 0 | 0.21 ± 0 |
| N | Gammagrass | 0.51 ± 0 | 0.37 ± 0.005 | 0.42 ± 0.005 |
|  | Sawdust | 0 ± 0 | 0.11 ± 0.11 | 0 ± 0 |
|  | Switchgrass | 1.69 ± 0 | 0.88 ± 0 | 0.725 ± 0.005 |
| N25 | Gammagrass | 0.23 ± 0 | 0.21 ± 0.005 | 0.06 ± 0 |
|  | Sawdust | 0 ± 0 | 0.04 ± 0 | 0 ± 0 |
|  | Switchgrass | 1.25 ± 0.005 | 0.59 ± 0 | 0.17 ± 0 |
| N50 | Gammagrass | 0.47 ± 0 | 0.3 ± 0.005 | 0.2 ± 0 |
|  | Sawdust | 0 ± 0 | 0.07 ± 0.02 | 0 ± 0 |
|  | Switchgrass | 2.13 ± 0 | 0.86 ± 0 | 0.28 ± 0 |

Further analysis of the effect of enzyme treatments on ethanol production for each substrate showed that in both switchgrass and gammagrass, the enzyme treatments had significant effects. In the case of sawdust, no ethanol was produced in any of the enzyme-treated samples, even after 48 h and 72 h of biomass saccharification. Ethanol conversion efficiencies for selected samples are presented in Table 17.

TABLE 17

Ethanol Conversion Efficiencies for SG2 Saccharified Feedstock Biomass

| Enzyme Treatment | Switchgrass (SG) Ethanol Production (g/L) | Switchgrass (SG) Conversion Efficiency (%) | Gammagrass (GG) Ethanol Production (g/L) | Gammagrass (GG) Conversion Efficiency (%) |
|---|---|---|---|---|
| N | 0.73 | 35 | 0.42 | 44 |
| N50 | 0.28 | 16.5 | 0.2 | 26 |
| N25 | 0.17 | 15 | 0.06 | 15 |
| C50N | 0.21 | 4 | — | — |
| C25N | 0.14 | 5 | — | — |

Example 4: Evaluation of Feedstock Concentration

In this example, the effect of acid-pretreated switchgrass feedstock concentration on saccharification by *Trichoderma* SG2 crude enzyme extract is examined Acid-pretreatment of switchgrass was carried out as described in Example 2. Acid-pretreated switchgrass was used at concentrations of 2, 5, 10, 15, and 20%. Crude enzyme production of *Trichoderma* SG2 and saccharification were carried out as described in Examples 1 and 2, except that different concentrations of acid-pretreated switchgrass were used in each treatment.

Overall, feedstock concentration had a significant effect with 10%>5%>2%>20%>15%. Fermentation time contributed significantly to glucose yield. Results for different feedstock concentrations and fermentation times are presented in Table 18.

TABLE 18

Saccharification of Acid-Pretreated Switchgrass

| Feedstock Concentration (w/v) | Incubation Time (Hours) | Glucose Production (g/L) | Xylose Production (g/L) |
|---|---|---|---|
| 2% | 24 | 7.97 ± 0.095 | 2.1 ± 0.08 |
|  | 48 | 9.03 ± 0.205 | 2.39 ± 0 |
|  | 72 | 9.4 ± 0.4 | 1.99 ± 0.31 |

TABLE 18-continued

Saccharification of Acid-Pretreated Switchgrass

| Feedstock Concentration (w/v) | Incubation Time (Hours) | Glucose Production (g/L) | Xylose Production (g/L) |
| --- | --- | --- | --- |
| 5% | 24 | 8.99 ± 0.18 | 2.35 ± 0.05 |
|  | 48 | 9.29 ± 0.28 | 2.4 ± 0.035 |
|  | 72 | 11.74 ± 0.07 | 2.7 ± 0.03 |
| 10% | 24 | 6.87 ± 0.18 | 2.23 ± 0.06 |
|  | 48 | 8.11 ± 0.28 | 2.43 ± 0.14 |
|  | 72 | 15.83 ± 0.07 | 3.84 ± 0.36 |
| 15% | 24 | 2.94 ± 0.085 | 1.4 ± 0.02 |
|  | 48 | 4.22 ± 0.68 | 1.92 ± 0.2 |
|  | 72 | 9.56 ± 1.14 | 2.92 ± 0.28 |
| 20% | 24 | 6.2 ± 0.29 | 2.41 ± 0.12 |
|  | 48 | 2.94 ± 0.92 | 1.42 ± 0.28 |
|  | 72 | 12.62 ± 4.73 | 3.39 ± 0.82 |

Within each concentration, glucose yield increased over time significantly only for 5%, 10%, and 15% feedstock concentrations. For xylose, different feedstock concentrations did not yield significantly different results. The highest glucose yield was 15.83 g/L; the corresponding xylose yield was 3.84 g/L. These occurred with a 10% switchgrass sample after 72 h of saccharification.

Of the five different feedstock concentrations tested, a 5% concentration resulted in the highest sugar yields upon saccharification with SG2 crude enzyme. Concentrations of 15% and 20% made the medium too thick. This did not allow for proper mixing and which resulted in final product had little or no liquid for sampling, resulting in high variation. The presence of liquid is vital for proper enzyme action on the feedstock.

Example 5: Scale-Up of Saccharification and Fermentation Processes

In this example, scale-up of acid-pretreated switchgrass saccharification by *Trichoderma* SG2 crude enzyme-commercial enzyme cocktail (C50N) and subsequent ethanol production is examined One liter of crude enzyme extract of *Trichoderma* SG2 was produced using optimized screening medium as described in Example 1. After incubation, broth was transferred into sterile 250 mL centrifuge tubes and centrifuged at 4000 rpm for 20 min; the supernatant from all tubes was pooled. This resulted in approximately 1 L of crude enzyme extract for further saccharification studies. Crude enzyme samples were assayed for cellulase, xylanase, β-glucosidase, and β-xylosidase activity as described Example 1.

Saccharification was carried out at 50° C. in a 5 L glass media bottle with an airtight cap. 1 L of SG2 crude enzyme extract was added to the bottle. Acid-pretreated switchgrass was added in either a 2% (20 g) or 5% (50 g) concentration. A commercial enzyme cocktail at 50% strength was also added to the 2% switchgrass feedstock. Aliquots were removed at 24 h intervals and analyzed for sugar release. Results from this scaled-up process are presented in Table 19. The maximum yields of glucose (4.96 g/L) and xylose (1.37 g/L) were obtained after 72 h saccharification. Using 2% switchgrass, 42% conversion of cellulose to glucose was achieved.

TABLE 19

Scaled-Up Saccharification of 2% Acid-Pretreated Switchgrass Using Treatment C50N (Crude Extract from SG2)

| Saccharification Time (Hours) | Glucose Production (g/L) | Xylose Production (g/L) |
| --- | --- | --- |
| 24 | 4.61 ± 0.07 | 1.2 ± 0.02 |
| 48 | 4.81 ± 0.07 | 1.27 ± 0.01 |
| 72 | 4.96 ± 0.04 | 1.37 ± 0.08 |

Ethanol fermentation was carried out on 72 h-saccharified switchgrass (2%, acid-pretreated) as described in Example 2. After 24 h ethanol fermentation, the ethanol yield was 2.0 g/L and residual glucose was 0.13 g/L. Ethanol at 48 h and 72 h was below detectable levels. Residual glucose and xylose levels were 0.13 and 1.19 g/L, respectively. The theoretical ethanol yield after 24 h fermentation was 2.53 g/L; actual yield was 2.0 g/L, which implies a conversion efficiency of about 80%. Results of ethanol fermentation are presented in Table 20.

TABLE 20

Ethanol Fermentation after Scaled-Up Saccharification (72 h) of 2% Acid-Pretreated Switchgrass

| | |
| --- | --- |
| Residual Glucose (g/L) | 0.13 ± 0.003 |
| Residual Xylose (g/L) | 1.19 ± 0.02 |
| Ethanol (g/L) | 2 ± 0.02 |

Using 5% acid-pretreated switchgrass, 6.4 g/L glucose and 1.7 g/L xylose were obtained after 72 h saccharification by SG2 crude enzyme only (Table 21).

TABLE 21

Scaled-Up Saccharification of 5% Acid-Pretreated Switchgrass Using Treatment C50N (Crude Extract from SG2)

| Saccharification Time (Hours) | Glucose Production (g/L) | Xylose Production (g/L) |
| --- | --- | --- |
| 24 | 5.57 ± 0.02 | 1.49 ± 0.02 |
| 48 | 6.47 ± 0.29 | 1.73 ± 0.07 |
| 72 | 6.44 ± 0.25 | 1.75 ± 0.07 |

Compositional analysis of the different biomass sources is provided in Table 22. This study yielded 12.8% glucose which was produced from about 60% cellulose, indicating 21% conversion of cellulose to glucose. Ethanol fermentation by *Saccharomyces cerevisiae* resulted in 2.84 g of ethanol after 24 h. 2.84 g of ethanol was released from 6.4 g glucose; the theoretical yield was 3.37 g. This represents an 84% conversion efficiency of ethanol from 5% switchgrass.

TABLE 22

Compositional Analysis of Different Biomass Feedstocks (Values in %)

| Biomass | Crude protein | Crude fiber | ADF | NDF | Ash | Cellulose | Lignin | Hemi-cellulose | Reducing sugars |
|---|---|---|---|---|---|---|---|---|---|
| Union Spring Switchgrass | 6.31 | 33.95 | 40.52 | 78.30 | 4.76 | 33.89 | 5.75 | 37.78 | 3.07 |
| Acid-treated Union Spring Switchgrass | 5.30 | 48.90 | 64.96 | 76.06 | 2.44 | 53.12 | 10.15 | 11.10 | 0.47 |
| Auburn Switchgrass | 2.55 | 43.31 | 51.69 | 83.53 | 1.48 | 41.59 | 9.97 | 31.84 | 1.42 |
| Acid-treated Auburn Switchgrass | 1.89 | 60.00 | 82.30 | 84.63 | 0.52 | 59.34 | 22.87 | 2.33 | 0.40 |
| Gammagrass | 5.64 | 35.41 | 46.97 | 74.94 | 3.05 | 34.53 | 11.29 | 27.98 | 1.03 |
| Acid-treated Gammagrass | 5.49 | 48.30 | 73.97 | 76.15 | 1.02 | 57.36 | 16.16 | 2.19 | 0.15 |
| Sawdust | 2.46 | 48.86 | 62.62 | 72.46 | 1.58 | 46.49 | 16.16 | 9.84 | 0.36 |
| Acid-treated Sawdust | 2.09 | 58.56 | 82.56 | 82.22 | 0.63 | 57.08 | 25.60 | 0.00 | 0.05 |

Example 6: Saccharification of Paper Powder

In this example, the effect of *Trichoderma* SG2 crude enzyme on the saccharification of paper powder is examined. Shredded office waste paper (white, printed) was milled using a Fritsch Pulverisette 16 mill at a 2 mm setting. Samples were stored in zip-top bags. Acid-pretreatment and heat (steam) pretreatment were performed according to the methods of Example 2. In this experiment, virgin (untreated) paper powder, heat-pretreated, and acid-pretreated samples were used at 2% and 5% for saccharification. Enzyme production, saccharification, and sugar estimation were carried out as described in Examples 1 and 2.

Sugar yields from autoclaved paper powder and virgin paper powder were negligible (<0.5 g/L after 24 h and no detectable sugars at and after 48 h). Yields from acid pretreated paper powder are provided in Table 23.

TABLE 23

Saccharification of 5% Acid-Pretreated Paper Powder (Crude Extract from SG2)

| Saccharification Time (Hours) | Glucose Production (g/L) | Xylose Production (g/L) |
|---|---|---|
| 24 | 8.5 | 2.7 |
| 48 | 10.32 | 3.9 |
| 72 | 10.25 | 3.7 |

Due to the yield of glucose from acid-pretreated paper powder at 5% concentration, it was determined that paper waste can be utilized for saccharification and potential biofuel production, for example as a supplement to switchgrass feedstock.

Example 7: Paper Powder Supplementation of Switchgrass Feedstock

In this example, the effect of paper powder supplementation of switchgrass feedstock on sugar yield by crude enzyme extract from *Trichoderma* SG2 was examined.

Feedstocks at 2, 4, 5, and 6% consisting of 1:1 mixtures of acid-pretreated switchgrass and acid-pretreated paper powder were used. Enzyme production, saccharification, and sugar estimation were carried out as described in Example 1.

Supplementation of switchgrass feedstock with paper powder resulted in glucose and xylose levels which were slightly higher than switchgrass feedstock alone (Table 24). At a total supplement concentration of 6% (3% paper powder and 3% switchgrass), the highest sugar yields (glucose and xylose) were obtained.

TABLE 24

Saccharification of Acid-Pretreated Switchgrass

| Feedstock Concentration (w/v) | Incubation Time (Hours) | Glucose Production (g/L) | Xylose Production (g/L) |
|---|---|---|---|
| 2% | 24 | 3.29 ± 0.17 | 1.64 ± 0.09 |
|  | 48 | 3.57 ± 0.12 | 1.8 ± 0.075 |
|  | 72 | 3.68 ± 0.14 | 1.88 ± 0.09 |
| 4% | 24 | 8.92 ± 0.88 | 2.73 ± 0.13 |
|  | 48 | 9.95 ± 0.97 | 3.27 ± 0.3 |
|  | 72 | 10.66 ± 1.2 | 3.61 ± 0.39 |
| 5% | 24 | 10.41 ± 0.88 | 3.27 ± 0.13 |
|  | 48 | 11.72 ± 0.34 | 3.76 ± 0.13 |
|  | 72 | 12.25 ± 0.15 | 4 ± 0.19 |
| 6% | 24 | 11.84 ± 0.34 | 3.57 ± 0.13 |
|  | 48 | 13.8 ± 0.03 | 4.1 ± 0.07 |
|  | 72 | 14.92 ± 0.21 | 4.4 ± 0 |

Example 8: Evaluation of Serial Enzyme Addition to Feedstock

In this example, repeated addition of crude *Trichoderma* SG2 enzyme extract to saccharified switchgrass was examined SG2 crude enzyme extract was prepared as described in Example 1; acid-pretreated switchgrass was used at 2% and 5% concentrations and the experiments were carried out in duplicate. Samples were treated with crude enzyme and, after 24 h, were centrifuged at 14,000 g for 15 min using a Beckman Coulter centrifuge. Supernatants were removed and collected for sugar analysis. Following this, fresh crude enzyme samples were added to the saccharified residues. These mixtures were transferred to flasks and allowed to saccharify for another 24 h. Repeated extractions were conducted so as to obtain data after 24 h, 48 h, and 72 h. Enzyme production, saccharification, and sugar estimation were carried out as described in Example 1; results are presented in Table 25.

TABLE 25

Repeated Saccharification of Switchgrass Feedstock

| Feedstock Concentration (w/v) | Incubation Time (Hours) | Glucose Production (g/L) | Xylose Production (g/L) |
| --- | --- | --- | --- |
| 2% | 24 | 6.26 ± 0.055 | 1.94 ± 0.05 |
|  | 48 | 1.14 ± 0.36 | 0.37 ± 0.26 |
|  | 72 | 0.05 ± 0.005 | 0 ± 0 |
| 5% | 24 | 7.93 ± 0.06 | 2.11 ± 0.01 |
|  | 48 | 4.99 ± 0.24 | 1.57 ± 0.13 |
|  | 72 | 0.27 ± 0.2 | 0.78 ± 0.08 |

Repeated saccharification of biomass does not enhance overall sugar yield as compared with one-time enzyme addition in the case of acid-pretreated switchgrass. Using 10 mL of crude enzyme extract in a one-time addition yields far greater sugar compared with 3×10 mL aliquots added at 24 h intervals. Marginal increases in sugar yield (e.g. with 5% switchgrass) are not proportional to the amount of enzyme used.

Example 9: Effects of Fungal Culture Age on Enzyme Activity and Saccharification In this example, the effects of *Trichoderma* SG2 culture age on enzyme activities and saccharification are examined.

Fresh potato dextrose agar (PDA) plates were streaked with *Trichoderma* SG2, incubated at 30° C. for one week for sporulation, and used for inoculation seed medium. Seed inoculum was incubated at 30° C. for 3 days and was used to inoculate screening medium. Three 250 mL flasks containing 50 mL of the screening medium were incubated at 30° C. for 5 days with shaking at 200 rpm. Samples were centrifuged at 5000 rpm and the supernatant was collected for determination of enzyme activities. This process was repeated after three months on the same culture to compare enzyme activities before and after extended storage.

The cellulase, xylanase, and β-xylosidase enzyme activities of SG2 increased slightly after three months, whereas β-glucosidase enzyme activity remained unchanged (Table 26), thus demonstrating that routine subculturing of *Trichoderma* SG2 does not significantly affect enzyme activities. SG2 subcultures from agar plates stored at 4° C. can be safely used for producing saccharifying enzymes, including in-house.

TABLE 26

Stability of Enzyme Production by Fresh and Three-Month-Old *Trichoderma* SG2

| Fungal Strain | Cellulase Activity (U/mL/30 min) | Xylanase Activity (U/mL/30 min) | β-Glucosidase Activity (U/mL/30 min) | β-Xylosidase Activity (U/mL/30 min) |
| --- | --- | --- | --- | --- |
| Fresh | 17.02 ± 0.001 | 57.02 ± 0.075 | 18 ± 0.006 | 16 ± 0.02 |
| 3 Months | 20.57 ± 0.002 | 64.6 ± 0.009 | 17.66 ± 0.009 | 25.84 ± 0.013 |

Similarly, the effect of culture age on saccharification was assessed. Two-month-old SG2 culture which had been grown on PDA and stored at 4° C. was used to inoculate seed flasks and enzyme production was carried out as described in Example 1. This enzyme is referred to as "old inoculum enzyme." A control culture (5-6 days old) was similarly treated and the enzyme referred to as "fresh inoculum enzyme." Enzyme age did not affect saccharification (Table 27).

TABLE 27

Saccharification of Acid-Pretreated Switchgrass

| Substrate and Enzyme Treatments | Incubation Time (Hours) | Glucose Production (g/L) | Xylose Production (g/L) |
| --- | --- | --- | --- |
| 2% Switchgrass + fresh inoculum enzyme | 24 | 6.57 ± 0.79 | 1.745 ± 0.195 |
|  | 48 | 7.22 ± 0 | 1.94 ± 0 |
|  | 72 | NA | NA |
| 2% Switchgrass + old inoculum enzyme | 24 | 3.16 ± 0.22 | 1.79 ± 0.05 |
|  | 48 | 7.11 ± 0.21 | 1.97 ± 0.04 |
|  | 72 | 7.39 ± 0.17 | 2.63 ± 0.06 |
| 5% Switchgrass + fresh inoculum enzyme | 24 | 8.015 ± 0.145 | 2.23 ± 0.22 |
|  | 48 | 8.3 ± 1.24 | 2.14 ± 0.28 |
|  | 72 | 9.62 ± 0 | 3.03 ± 0 |
| 5% Switchgrass + old inoculum enzyme | 24 | 7.91 ± 0.175 | 2.14 ± 0.09 |
|  | 48 | 8.72 ± 0.025 | 2.2 ± 0 |
|  | 72 | 7.37 ± 2.38 | 2.56 ± 0.55 |
| 10% Switchgrass + fresh inoculum enzyme | 24 | 7.06 ± 0.87 | 2.76 ± 0.02 |
|  | 48 | 4.57 ± 0.56 | 1.87 ± 0.13 |
|  | 72 | 6.14 ± 1.5 | 2.64 ± 0.36 |
| 10% Switchgrass + old inoculum enzyme | 24 | 5.19 ± 0.62 | 2.09 ± 0.005 |
|  | 48 | 6.42 ± 0.93 | 2.02 ± 0.06 |
|  | 72 | 4.94 ± 0.77 | 2.41 ± 0.08 |

NA: Not available.

Example 10: Sand Filtration to Separate Fungal Biomass from Crude Enzyme Extract In this example, the use of sand filtration for separating fungal biomass from crude enzyme extract is examined Crude enzyme production from *Trichoderma* SG2 cultures was carried out in ten 250 mL flasks containing optimized screening medium as discussed previously. Each flask contained 100 mL medium and was sterilized at 121° C. for 1 h before inoculation. 10% of 72 h inoculum was added aseptically into each flask. Flasks were incubated at 30° C. for 5 days. On the fifth day of enzyme production, broth from all 10 flasks was pooled and stored at 4° C. to prevent enzyme activity during filtration. Of 1 L broth, 300 mL was used for sand filtration, 100 mL for centrifugation, a small portion for enzyme assays, and the rest stored at 4° C. Centrifugation served as a control; in this step, 100 mL of broth was transferred into sterile 50 mL centrifuge tubes and centrifuged at 5000 rpm for 10 min.

A sand column (1.5 cm diameter, 15 cm length) for filtration was prepared by loading 100 g of 40-100 mesh acid-washed sand into borosilicate glass columns with polyethylene bed support. Each experiment was performed in triplicate. 100 mL of the cold fungal broth was loaded onto the column and the filtrate was collected in a sterile centrifuge tube placed in an ice bath. The collected sample was used for enzyme assays and for saccharification. Enzyme assays and saccharification of 5% acid-pretreated switchgrass were carried out as described earlier. For saccharification, two replicates were performed for each treatment.

Enzyme activities and sugar yields for centrifuged and sand-filtered samples were similar (Table 28). Sand filtration is an inexpensive and effective method for separating fungal biomass from crude enzyme and can be employed as part of a "farm-deployable" bioreactor process for cellulosic ethanol production.

TABLE 28

Comparison of Sand-Filtered and Centrifuged Crude Enzyme from *Trichoderma* SG2

| | Centrifuged | Sand-Filtered |
|---|---|---|
| Cellulase Activity (U/mL/30 min) | 11.97 ± 0.003 | 12.7 ± 0.002 |
| Xylanase Activity (U/mL/30 min) | 39 ± 0.004 | 46.7 ± 0.012 |
| β-Glucosidase Activity (U/mL/30 min) | 19 ± 0.004 | 18 ± 0.004 |
| β-Xylosidase Activity (U/mL/30 min) | 6.8 ± 0.01 | 6 ± 0.007 |
| Glucose Yield (g/L) | 6.97 ± 0.003 | 6.33 ± 0.002 |
| Xylose Yield (g/L) | 2.1 ± 0.004 | 1.1 ± 0.012 |
| Protein (mg/mL) | 0.83 | 0.63 |

Example 11: Improved Pretreatment Methods Using Combinations of Acid and Alkali In this example, the use of different combinations of acid and/or alkali for pretreatment of switchgrass is examined.

At least eight different pretreatment strategies were evaluated for switchgrass: 2% acid followed by 2% alkali, 2% alkali followed by 2% acid, 2% acid only, 2% alkali only, 0.5% acid only, 0.5% acid followed by 0.5% acid, 85% acid followed by acetone, and 85% acid followed by ethanol.

For pretreatments involving 0.5% acid and 2% acid or 2% alkali, sulfuric acid and sodium hydroxide were used. About 100 g of switchgrass was soaked in respective acid or alkali solution and autoclaved at 121° C. for 30 min with slow exhaust. After autoclaving the contents were allowed to cool to room temperature, liquid drained using a finely woven white canvas tote cloth and the pretreated switchgrass washed several times with water to completely remove any residues. After 4-5 washes the pH of the liquid was tested and was washed further if the pH was lower than 5. The washed switchgrass was dried at room temperature for 72 h and stored in airtight zip-top bags until further use.

For acid followed by alkali pretreatment (Acid-Alkali), 10% switchgrass was soaked in 2% sulfuric acid and autoclaved at 121° C. for 30 min. After autoclaving samples were washed several times with running water until the pH reached 5-6. Samples were then soaked in 2% sodium hydroxide and autoclaved at 121° C. for 30 min. After autoclave the samples were washed thoroughly until the pH reached 5-6 range and the samples were air dried at room temperature for 72 h. A similar procedure was followed for 2% alkali followed by 2% acid (Alkali-Acid).

For sequential mild acid pretreatment, samples were first treated with 0.5% sulfuric acid as outlined above and followed by second pretreatment with 0.5% acid after removing first residue.

For phosphoric acid pretreatment, 13.125 g of switchgrass was mixed with 100 mL of 85% phosphoric acid and maintained at 50° C. in a water bath at 1 atmosphere pressure for 60 min. The reaction was terminated by adding 250 mL of 95% ethanol. The samples were centrifuged at 4500 rpm at room temperature for 10 min. The pellet was resuspended in 250 mL of 95% ethanol, followed by centrifugation at 4500 rpm for 10 min and the pellet was washed with deionized water 3-4 times until the pH reached 5-6. The same method was carried out with 85% phosphoric acid followed by pure acetone instead of ethanol.

Crude *Trichoderma* SG2 enzyme was produced and saccharification of pretreated switchgrass was carried out as described previously.

Results for saccharification of switchgrass with different pretreatments are presented in Table 29. With respect to glucose yield after 72 h saccharification by SG2 crude enzyme was concerned, the highest value was 5.4 g/L and was obtained with 85% phosphoric acid-acetone treatment. Interestingly, both the 85% phosphoric acid-alcohol and the 2% alkali-2% acid methods yielded around 4.6 g/L sugar. The previously optimized pretreatment for switchgrass was 2% sulfuric acid alone which yielded 2 g/L sugar upon saccharification by SG2 crude enzyme. For xylose, the highest yield of was measured in samples that had been subjected to the 2% alkali-2% acid treatment.

TABLE 29

*Trichoderma* SG2 Crude Enzyme Saccharification of 2% Switchgrass Subjected to Different Pretreatments

| Treatment | 24 h | 48 h | 72 h |
|---|---|---|---|
| Glucose Yield (g/L) | | | |
| 2% $H_2SO_4$—2% NaOH | 1.384 ± 0.001 | 2.375 ± 0.001 | 2.375 |
| 2% NaOH—2% $H_2SO_4$ | 3.818 ± 0.001 | 4.717 ± 0.006 | 4.717 |
| 2% $H_2SO_4$ | 1.780 ± 0.001 | 2.070 ± 0.0006 | 2.070 |
| 2% NaOH | 0.540 ± 0.002 | 0.172 ± 0.0001 | 0.172 |
| 0.5% $H_2SO_4$ | 1.831 ± 0.002 | 2.027 ± 0.003 | 2.027 |
| 0.5% $H_2SO_4$—0.5% $H_2SO_4$ | 1.936 ± 0.001 | 2.283 ± 0.0008 | 2.283 |
| 85% Phosphoric acid-pure Acetone | 5.280 ± 0.001 | 5.280 ± 0.001 | 5.370 |
| 85% Phosphoric acid-95% ethanol | 2.211 ± 0.02 | 4.425 ± 0.01 | 4.618 |
| Xylose Yield (g/L) | | | |
| 2% $H_2SO_4$—2% NaOH | 0.485 ± 0.001 | 0.548 | 0.548 |
| 2% NaOH—2% $H_2SO_4$ | 2.139 ± 0.004 | 2.345 ± 0.003 | 2.345 |
| 2% $H_2SO_4$ | 0.679 ± 0.003 | 0.767 ± 0.001 | 0.767 |
| 2% NaOH | 1.093 ± 0.003 | 1.485 ± 0.001 | 1.485 |
| 0.5% $H_2SO_4$ | 0.921 | 1.010 ± 0.003 | 1.010 |
| 0.5% $H_2SO_4$—0.5% $H_2SO_4$ | 0.816 ± 0.001 | 0.982 ± 0.04 | 0.982 |
| 85% Phosphoric acid-pure Acetone | 0.836 ± 0.008 | 0.836 ± 0.01 | 0.863 |
| 85% Phosphoric acid-95% ethanol | 0.352 ± 0.01 | 0.701 ± 0.02 | 0.723 |

Example 12: Use of Mixtures of Pretreatment Liquor Streams for pH Adjustment in Formulation of Media for Microbial Growth and Production of Microbial Products Pre-treatment liquor contains sugars and other nutrients that support microbial growth. Liquors from sequential acid and alkali pre-treatment were combined to adjust pH to favor microbial production of different products (e.g., enzymes, alcohols such as butanol and ethanol, etc.).

100 g of pulverized switchgrass was suspended in 1 L of 0.5% NaOH and subjected to autoclaving at 121° C. (15 psi) for 20 min. After cooling to room temperature, the NaOH pretreatment liquor was removed by filtering through a sheet of burlap. The resulting liquor is hereafter referred to "NaOH pretreatment liquor (NaOH-PTL)." Residual liquor was manually squeezed out into a collection tray. Biomass solids were washed twice by re-suspending in 500 mL of 0.5% sulfuric acid each time and removing the acid liquor through a sheet of burlap. The waste resulting from the two wash cycles is hereafter referred to "acid wash waste ($H_2SO_4$-WL)." Washed biomass residue was then re-suspended in 500 mL of 0.5% sulfuric acid and subjected to autoclaving and filtration as described above. The resulting waste is hereafter referred to as "acid pretreatment liquor ($H_2SO_4$-PTL)."

The pre-treatment liquors were combined in the ratios provided in Table 30. Initial pH and reducing sugar concentrations were determined. 50 mL of each liquor were transferred to a 250 mL flask, sterilized by autoclaving (121° C., 20 min), and cooled to room temperature. Two agar plugs of a confluent agar culture of *Trichoderma* sp. SG2 were used to inoculate the sterile medium in triplicate. The culture was incubated at 30° C. for 4 days with orbital shaking (200 rpm).

Enzyme production with a combination of pretreatment waste and enzyme production mineral medium was also examined. The pre-treatment liquors were combined at the ratios provided in Table 30 and were then mixed at a 1:1 ratio with either distilled water (control) or enzyme production medium (2 g peptone, 0.5 g yeast extract, 0.5 g polysorbate 80, 2 g $KH_2PO_4$, 1.2 g $(NH_4)_2SO_4$, 0.5 g $MgSO_4 \cdot 7H_2O$, 0.1 g $CaCl_2$, 0.003 g $FeSO_4 \cdot 7H_2O$, and 2 mL of Fotch mineral element solution per liter of medium). 50 mL of these mixtures was transferred to a 250 mL Erlenmeyer flask and sterilized by autoclaving at 121° C. for 20 min. After cooling to room temperature, flasks were inoculated with two potato dextrose agar (PDA) culture plugs (1.25 cm) of *Trichoderma* SG2 culture and incubated at 30° C. with orbital shaking (200 rpm). Inoculum was prepared by inoculating the center of PDA with a piece of PDA culture of *Trichoderma* SG2 and incubating at 30° C. for 3 days; inocula were preserved at 4° C. for not more than six weeks prior to use.

TABLE 30

Production of Cellulase and Xylanase in Mixtures of Sequential Alkali and Acid Pretreatment Liquor

| Pre-treatment liquor mixtures | Cellulase (U/mL/ 30 min) | Xylanase (U/mL/ 30 min) |
|---|---|---|
| 0.5% NaOH-PTL (pH 9.2) mixed with 0.5% $H_2SO_4$-WL (pH 1.7) at a ratio of 1:1 (pH 4.6) | 0.71 ± 0.10 | 3.23 ± 0.43 |
| 0.5% NaOH-PTL (pH 9.2) mixed with 0.5% $H_2SO_4$-PTL (pH 1.6) at a ratio of 3:2 (pH 4.1) | 1.47 ± 0.17 | 3.61 ± 0.21 |
| 0.5% NaOH-PTL (pH 9.2) mixed with 0.5% $H_2SO_4$-WL (pH 1.7) at a ratio of 1:1; and diluted 50% with distilled water | 0.91 ± 0.06 | 4.08 ± 0.37 |
| 0.5% NaOH-PTL (pH 9.2) mixed with 0.5% $H_2SO_4$-PTL (pH 1.6) at a ratio of 3:2; and diluted 50% with distilled water | 0.65 ± 0.06 | 3.44 ± 0.22 |
| 0.5% NaOH-PTL (pH 9.2) mixed with 0.5% $H_2SO_4$-PTL (pH 1.6) at a ratio of 3:2; and diluted 50% with enzyme production medium | 4.39 ± 0.74 | 31.66 ± 2.19 |
| 0.5% NaOH-PTL (pH 9.2) mixed with 0.5% $H_2SO_4$-PTL (pH 1.6) at a ratio of 3:2; and diluted 50% with enzyme production medium (boiled to inactivate enzyme) | 3.89 ± 0.135 | 15.11 ± 0.85 |

In general, all the mixtures of alkali and acid pretreatment liquors supported the growth *Trichoderma* SG2 and production of significant levels of cellulolytic and xylanolytic enzymes. The addition of enzyme production mineral medium further supported microbial growth; boiled enzyme culture filtrate decreased enzyme activity.

Example 13: Comparison of β-Glucosidase and β-Xylosidase Activities of *Trichoderma* SG2 and SG4 with the Improved Mutant *Trichoderma reesei* RUT-C30 Used for Industrial Production of Cellulolytic and Xylanolytic Enzymes The β-glucosidase and β-xylosidase activities of *Trichoderma* SG2, SG4, and RUT-C30 were compared. Enzyme production medium was prepared as in Example 12. In independent parallel experiments, 50 mL of medium was placed in 250 mL flasks to which either 0.25 g shredded waste paper or 0.25 g of pulverized switch grass and autoclaved at 121° C. for 20 min. Sterile media was inoculated with agar plugs (1.25 cm diameter) obtained from Sabouraud-CMC agar plate cultures of each microbial isolate that had been incubated at 30° C. for 5 days. Cultures prepared in this way were incubated with orbital shaking (200 rpm) at 30° C. for 12 days with sampling every 3 days. Fungal biomass was removed from cultures by centrifugation and supernatants were used to determine enzyme activities. Results are presented in Table 31.

TABLE 31

β-glucosidase and β-xylosidase Activities of *Trichoderma* SG2, SG4, and RUT-C30 Cultures

| Strain | Time (Days) | β-glucosidase (U/mL/30 min) | β-xylosidase (U/mL/30 min) |
|---|---|---|---|
| SG2 | 3 | 27.00 ± 8.38 | 8.35 ± 0.29 |
|  | 6 | 31.40 ± 4.98 | 10.17 ± 1.01 |
|  | 8 | 34.17 ± 1.67 | 12.74 ± 0.83 |
|  | 12 | 35.87 ± 1.12 | 11.22 ± 1.66 |
| SG4 | 3 | 23.74 ± 3.17 | 10.19 ± 2.54 |
|  | 6 | 30.24 ± 0.53 | 10.94 ± 1.53 |
|  | 8 | 37.22 ± 3.20 | 10.20 ± 1.52 |
|  | 12 | 35.12 ± 3.72 | 9.37 ± 1.23 |
| RUT-C30 | 3 | 5.95 ± 1.92 | 4.75 ± 1.23 |
|  | 6 | 9.92 ± 2.03 | 5.47 ± 0.53 |
|  | 8 | 13.27 ± 1.48 | 5.54 ± 0.08 |
|  | 12 | 15.13 ± 2.71 | 5.74 ± 0.50 |

*Trichoderma* strains SG2 and SG4 displayed much higher production of β-glucosidase (2-5 orders of magnitude) and β-xylosidase (2 orders of magnitude) than the industrial strain RUT-C30; this varied somewhat with incubation time. As a hypercellulolytic mutant, however, RUT-C30 produced more cellulase than SG2 and SG4. All three strains produced comparable levels of xylanase activity.

Example 14: Co-Production of Cellulolytic, Xylanolytic, and Amylolytic Enzymes for Co-Saccharification of Mixtures of Lignocellulose Biomass by *Trichoderma* SG2

*Trichoderma* SG2 cultures were analyzed for the ability to co-produce cellulase, xylanase, and amylase. Culture medium was prepared as described in Example 12. In independent parallel experiments, 50 mL of medium was added to a 250 mL Erlenmeyer flask. 0.25 g of pulverized switch grass (particle size≤2 mm) and 0.25 g of paper powder (particle size≤2 mm) were added to each flask. 0.25 g of soluble starch were also added to some flasks. Flasks were plugged with foam plugs and sterilized by autoclaving as previously described. Culture procedures were followed as described in Examples 12 and 13. After 5 days, cell-free culture supernatant containing enzymes was recovered by centrifugation and enzyme activities were determined. Results are presented in Table 32.

TABLE 32

Co-production of Cellulolytic, Xylanolytic, and Amylolytic
Enzymes (U/mL/30 min) by *Trichoderma* SG2

| Enzyme | Activity in Switchgrass/Paper Powder/Starch (SPS) Medium | Activity in Switchgrass/Paper Powder (SP) Medium |
|---|---|---|
| Cellulase | 5.168 ± 0.492 | 7.316 ± 0.575 |
| Xylanase | 28.155 ± 3.310 | 32.707 ± 1.859 |
| Amylase | 31.965 ± 3.125 | 14.394 ± 2.416 |

Significant co-production of amylolytic activity occurred along with cellulolytic and xylanolytic activity.

Example 15: Co-Saccharification of Switchgrass and Starch

The effects of starch on the saccharification of switchgrass were assessed. Reaction mixtures consisted of 0.1 g pretreated switchgrass, 1 g of 20% soluble starch solution gelatinized by autoclaving, 5.0 mL of enzyme (cell-free culture supernatant produced from a lignocellulosic medium lacking starch), 100 µL of metal ion stock, and 50 µL of 200 mg/L LACTROL®. This mixture was placed in 15 mL centrifuge tubes. A control experiment was run with distilled water instead of enzyme mixture. A second control involved the same reaction mixture, but omitting the starch. Reactions were incubated at 50° C. in an orbital incubator (80 rpm) for 24 hours. Results are presented in Table 33. Reducing sugar yield was determined by the DNS (3,5-dinitrosalicylic acid) method.

TABLE 33

Co-saccharification of Switchgrass and Starch using
*Trichoderma* SG2

| Substrate | Reducing Sugars (g/L) |
|---|---|
| Switchgrass (20 g/L) + Starch (20 g/L) | 8.001 ± 0.756 |
| Switchgrass (20 g/L) | 6.155 ± 0.278 |
| Starch (20 g/L) | 2.543 ± 0.209 |

The addition of starch to lignocellulosic saccharification displayed an additive effect; total reducing sugar yield increased compared to the saccharification of switchgrass or starch, alone.

Example 16: Addition of Metal Ions to Biomass Saccharification Reaction Mixture Promotes Biomass Saccharification Enzymes were produced as described above. Assay mixtures for enzymes were described as in Examples 12 and 13 except that 20 µL of a 500 mM stock solution of metal ions and surfactants was added to the reaction flasks, to a final concentration of 10 mM. Metals analyzed included barium, cobalt, calcium, iron, potassium, manganese, and zinc.

Switchgrass biomass that had been sequentially pretreated with 1% NaOH and autoclaved at 121° C. for 20 min, followed by 1% sulfuric acid with autoclaving was used to assess saccharification in the presence of metal ions.

In one experiment, the reaction mixture consisted of 0.2 g of pretreated switchgrass, 10 mL of enzyme (cell-free culture supernatant produced as described above), 200 µL of metal ion stock, and 100 µL of a 200 mg/L solution of LACTROL® in a 125 mL Erlenmeyer flask. A control was conducted in which the enzyme was replaced with distilled water. In another experiment, the reaction mixture consisted of 0.1 g of pretreated switchgrass, 5.0 mL of enzyme, 100 µL of metal ion stock, and 50 µL of 200 mg/L LACTROL® in a 15 mL centrifuge tube. Again, a control was conducted in which the enzyme was replaced with distilled water.

Reactions were incubated at 50° C. in an orbital incubator (80 rpm) for 24 h. When the reaction was carried out in 15 mL tubes, the tubes were placed horizontally on the shaker. Post-incubation, 100 µL of digest was diluted with 900 µL of deionized water and reducing sugar content was determined by the DNS method.

Barium, calcium, cobalt, iron, potassium, manganese, and zinc stimulated cellulolytic and xylanolytic activities compared to controls run without metal ions. The highest stimulatory effect was observed with manganese, followed by iron and barium. Metal ions, when added singly or in combination to biomass saccharification reaction mixtures, strongly promote fermentable sugar yield.

Example 17: Effect of Dilution of Enzymes on Cellulase, Xylanase, and Amylase Activities Enzyme (cell-free culture filtrate) of *Trichoderma* SG2 (PTA-120389) grown in lignocellulosic medium was diluted to 50% strength, to 25% strength, or to 10% strength using 50 mM sodium acetate buffer at pH 5.0. Cellulase, xylanase, and amylase activities were then determined for each dilution. Experimental procedures were followed as described above. Results are presented in Table 34.

TABLE 34

Effect of Enzyme Dilution on Total Cellulase, Xylanase, and
Amylase Activities of *Trichoderma* SG2

| Enzyme | Dilution | Activity (Units/mL/30 min) | Relative Activity |
|---|---|---|---|
| Cellulase | 100% | 9.838 ± 1.122 | 100 |
|  | 50% | 16.864 ± 1.314 | 171.4 |
|  | 25% | 26.129 ± 2.474 | 265.6 |
|  | 10% | 52.541 ± 1.050 | 534.1 |
| Xylanase | 100% | 48.017 ± 2.529 | 100 |
|  | 50% | 95.294 ± 6.317 | 198.5 |
|  | 25% | 175.109 ± 14.482 | 364.7 |
|  | 10% | 405.649 ± 23.989 | 844.8 |
| Amylase | 100% | 25.732 ± 0.543 | 100 |
|  | 50% | 45.523 ± 0.420 | 176.9 |
|  | 25% | 84.488 ± 0.502 | 328.3 |
|  | 10% | 195.882 ± 0.972 | 761.2 |

As can be seen above, more enzymes are present in the cell-free culture supernatant than are required to convert the various substrates to fermentable sugars. Thus, levels of enzyme and substrate can be varied to achieve maximum saccharification.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A spent biomaterial produced by the method comprising
   a. culturing a fungal strain comprising *Trichoderma* SG2, *Trichoderma* SG4, or a combination thereof, in culture medium, in the presence of a lignocellulosic medium and a starch to produce an enzyme composition and a spent biomaterial; and
   b. separating the spent biomaterial from the enzyme composition.

2. The biomaterial of claim 1, wherein when the fungal strain is *Trichoderma* SG2 or SG4 and the enzyme composition comprises cellulase, xylanase, beta-glucosidase, beta-xylosidase, amylase, or any combination thereof.

3. The biomaterial of claim 1, wherein the starch comprises an expired food product selected from the group consisting of corn starch, potato starch, rice starch, tapioca starch, bread or other bakery products, bread waste, bakery waste, donuts, donut waste, and any combination thereof.

4. The biomaterial of claim 1, wherein the enzyme composition is separated from the spent material by filtration or centrifugation.

5. The biomaterial of claim 1, wherein the biomaterial comprises *Trichoderma* SG2, *Trichoderma* SG4, or a combination thereof.

6. The composition of claim 1, wherein *Trichoderma* SG2, *Trichoderma* SG4, or a combination thereof is cultured in the presence of a lignocellulosic medium and a starch.

7. An animal feed comprising the spent biomaterial of claim 1.

8. A composition for improving plant health comprising the biomaterial of claim 1.

9. A method for remediating soil comprising applying the spent biomaterial of claim 1 to the soil.

10. An enzyme composition produced by culturing a fungal strain comprising *Trichoderma* SG2, *Trichoderma* SG4, or a combination thereof, in the presence of a lignocellulosic medium and a starch.

11. The composition of claim 10, wherein when the fungal strain is *Trichoderma* SG2 or SG4 and the enzyme composition comprises cellulase, xylanase, beta-glucosidase, beta-xylosidase, amylase, or any combination thereof.

12. The composition of claim 10, wherein the starch comprises an expired food product selected from the group consisting of corn starch, potato starch, rice starch, tapioca starch, bread or other bakery products, bread waste, bakery waste, donuts, donut waste, or any combination thereof.

* * * * *